US011824937B2

(12) United States Patent
Goodman

(10) Patent No.: US 11,824,937 B2
(45) Date of Patent: Nov. 21, 2023

(54) SYSTEM AND METHOD FOR HANDLING THE CONNECTION OF USER ACCOUNTS TO OTHER ENTITIES

(71) Applicant: Rissana, LLC, St. Louis, MO (US)

(72) Inventor: Micah Stone Goodman, Cambridge, MA (US)

(*) Notice: Subject to any disclaimer, the term of this patent is extended or adjusted under 35 U.S.C. 154(b) by 0 days.

(21) Appl. No.: 17/712,218

(22) Filed: Apr. 4, 2022

(65) Prior Publication Data

US 2022/0321658 A1  Oct. 6, 2022

Related U.S. Application Data

(60) Provisional application No. 63/170,535, filed on Apr. 4, 2021.

(51) Int. Cl.
| | | |
|---|---|---|
| *H04L 67/12* | (2022.01) |
| *G16H 80/00* | (2018.01) |
| *H04L 9/40* | (2022.01) |
| *H04L 67/306* | (2022.01) |
| *G16H 10/60* | (2018.01) |

(52) U.S. Cl.
CPC ............. *H04L 67/12* (2013.01); *G16H 10/60* (2018.01); *G16H 80/00* (2018.01); *H04L 63/102* (2013.01); *H04L 67/306* (2013.01)

(58) Field of Classification Search
CPC ..... H04L 67/12; H04L 63/102; H04L 67/306; H04L 63/105; H04L 63/10; G16H 10/60; G16H 80/00; G16H 20/00
See application file for complete search history.

(56) References Cited

U.S. PATENT DOCUMENTS 7,062,274 B2 * 6/2006 Shell .................. H04L 41/0886
                                                    455/445
8,321,239 B2    11/2012 Hasan
(Continued)

OTHER PUBLICATIONS

Top 10 mobile apps for personal medical records, Dr. Hempel Digital Health Network, Jul. 30, 2018, pp. 1-12, available at https://www.dr-hempel-network.com/digital-health-technolgy/top-10-mobile-apps-for-personal-medical-records/.
(Continued)

*Primary Examiner* — Javier O Guzman
(74) *Attorney, Agent, or Firm* — Greenberg Traurig, LLP

(57) ABSTRACT

User accounts can form any number of connections to any number of entities, enabling dynamic application functionality and data interaction regarding the user account and the connected entities. As a result, an individual can utilize the same user account and same application to access support from many entities. Entities may include social service organizations, groups of healthcare facilities, clinicians, medical devices, and other sources of support. The connection of a user account to an entity, updates the operations of the associated application system. For example, permissions regarding the transmission and modification of certain data associated with the user account and/or entity may be updated. Additionally, there may be additional functionality within software applications associated with the user account. There may be multiple possible forms of connections between a user account and a given entity, with each connection resulting in different outcomes. Connections can be removed and re-established as necessary.

33 Claims, 16 Drawing Sheets

(56) References Cited

U.S. PATENT DOCUMENTS

| | | | | |
|---|---|---|---|---|
| 8,407,205 | B2 | 3/2013 | Doshi | |
| 8,468,033 | B2 | 6/2013 | Gunn | |
| 8,543,421 | B2 | 9/2013 | Menschik | |
| 8,606,593 | B1 | 12/2013 | Green, III | |
| 8,650,045 | B2 | 2/2014 | Baldock | |
| 8,688,466 | B2 | 4/2014 | Kharraz Tavakol | |
| 8,768,725 | B2 | 7/2014 | Lorsch | |
| 8,984,017 | B2 | 3/2015 | Naeymi-Rad | |
| 8,990,834 | B2 | 3/2015 | Mathur | |
| 9,026,531 | B2 | 5/2015 | Hoffman | |
| 9,715,555 | B2 | 7/2017 | Doshi | |
| 9,817,559 | B2 | 11/2017 | Simon | |
| 9,992,292 | B2 | 6/2018 | Gunnarsson | |
| 10,257,814 | B2 * | 4/2019 | Baker | H04L 1/0031 |
| 10,305,882 | B2 * | 5/2019 | Hinton | H04L 63/0815 |
| 10,475,018 | B1 * | 11/2019 | Hitchcock | G06Q 20/227 |
| 10,566,090 | B2 | 2/2020 | Ivanoff | |
| 10,645,076 | B1 * | 5/2020 | Carson | H04L 63/0815 |
| 10,713,230 | B2 | 7/2020 | Weissman | |
| 10,748,645 | B2 | 8/2020 | Moturu | |
| 10,805,280 | B2 * | 10/2020 | Uchiyama | H04L 63/0815 |
| 10,862,890 | B2 * | 12/2020 | Gulbrandsen | G06F 16/955 |
| 10,902,942 | B1 | 1/2021 | Hames | |
| 10,986,071 | B2 | 4/2021 | McFarland | |
| 11,025,622 | B2 | 6/2021 | Pardehpoosh | |
| 11,056,230 | B2 | 7/2021 | Leszczuk | |
| 11,387,987 | B2 | 7/2022 | Carver | |
| 11,501,221 | B2 | 11/2022 | Kharraz-Tavakol | |
| 2002/0095499 | A1 * | 7/2002 | Barnett | H04L 67/306 709/226 |
| 2006/0106645 | A1 | 5/2006 | Bergelson | |
| 2007/0203754 | A1 | 8/2007 | Harrington | |
| 2008/0014931 | A1 * | 1/2008 | Yared | H04L 63/0815 455/432.3 |
| 2008/0320576 | A1 * | 12/2008 | Curling | H04L 63/0815 726/8 |
| 2012/0065989 | A1 | 3/2012 | Massoumi | |
| 2012/0109679 | A1 | 5/2012 | Massoumi | |
| 2013/0010935 | A1 * | 1/2013 | Lurie | H04M 15/00 379/88.01 |
| 2013/0035946 | A1 | 2/2013 | Ratan | |
| 2013/0067594 | A1 * | 3/2013 | Kantor | H04L 63/0838 726/28 |
| 2013/0086669 | A1 * | 4/2013 | Sondhi | H04W 12/068 726/8 |
| 2013/0325509 | A1 | 12/2013 | McCarrick | |
| 2014/0157434 | A1 * | 6/2014 | Graves | H04L 63/102 726/28 |
| 2014/0214442 | A1 | 7/2014 | Duffy | |
| 2015/0213198 | A1 | 7/2015 | Groys | |
| 2015/0324525 | A1 | 11/2015 | Saffran | |
| 2015/0334108 | A1 * | 11/2015 | Khalil | H04L 63/0815 726/8 |
| 2015/0356250 | A1 | 12/2015 | Polimeni | |
| 2016/0171226 | A1 | 6/2016 | Wu | |
| 2016/0180045 | A1 * | 6/2016 | Syed | G16H 10/60 705/2 |
| 2016/0210427 | A1 | 7/2016 | Mynhier | |
| 2016/0342741 | A1 | 11/2016 | Chin | |
| 2017/0078272 | A1 * | 3/2017 | Guionneau | H04L 63/0815 |
| 2018/0082022 | A1 | 3/2018 | Francois | |
| 2019/0164650 | A1 | 5/2019 | Schwartz | |
| 2019/0172590 | A1 | 6/2019 | Vesto | |
| 2019/0244683 | A1 | 8/2019 | Francois | |
| 2019/0295698 | A1 | 9/2019 | Doni | |
| 2020/0099740 | A1 | 3/2020 | Ben-Kiki | |
| 2020/0161003 | A1 | 5/2020 | Wright | |
| 2020/0219184 | A1 | 7/2020 | Robbin | |
| 2020/0350076 | A1 | 11/2020 | Ahrens | |
| 2020/0411181 | A1 * | 12/2020 | Agnello | G16H 40/67 |
| 2021/0407695 | A1 | 12/2021 | Morefield | |
| 2022/0005581 | A1 | 1/2022 | Brown | |

OTHER PUBLICATIONS

ERECOVERY: Preventing Relapse through Connections, Engagement, and Data, CHESS Health website, 2017, p. 1. available at https://www.chess.health/wp-content/uploads/2018/11/che-ss-eRecovery-EM181017.pdf.

* cited by examiner

| Record Index | Account Identifier | Entity Identifier | Connection Status |
|---|---|---|---|
| 1 | 31 | 45 | Accepted |
| 2 | 31 | 6 | Pending |
| 3 | 87 | 307 | Canceled |

*FIG. 2*

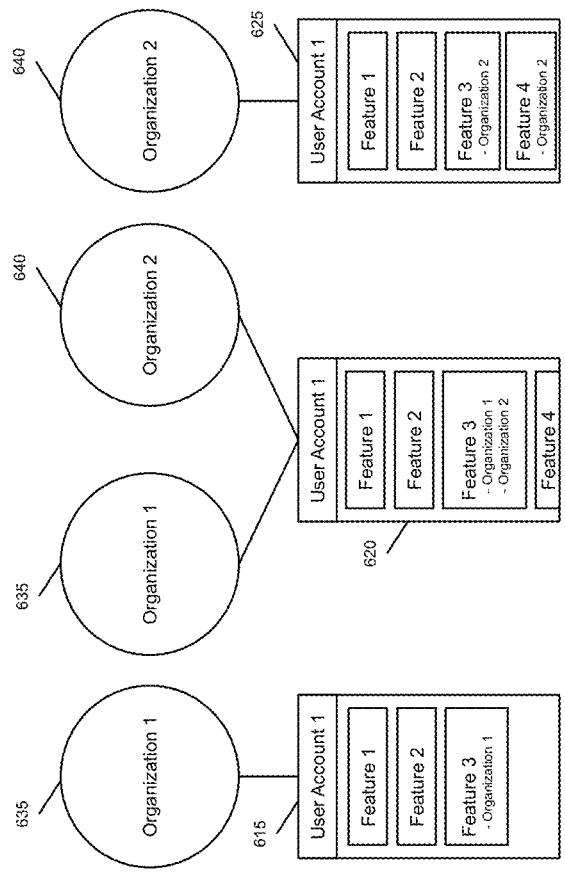

SYSTEM AND METHOD FOR HANDLING THE CONNECTION OF USER ACCOUNTS TO OTHER ENTITIES

CROSS-REFERENCE TO RELATED APPLICATION

This application claims priority under 35 U.S.C. § 119 to U.S. Patent Application No. 63/170,535 filed Apr. 4, 2021, entitled "SYSTEM FOR SOFTWARE ACCOUNTS THAT CAN BE CONNECTED AND DISCONNECTED FROM ANY NUMBER OF ENTITIES," the entire contents of which are incorporated herein by reference.

STATEMENT REGARDING FEDERALLY SPONSORED RESEARCH OR DEVELOPMENT

This invention was made with government support under 1R41DA050232-01 awarded by the National Institutes of Health. The government has certain rights in the invention.

BACKGROUND OF THE INVENTION

The process for addressing many healthcare concerns, especially mental and behavioral health conditions, rarely begins with seeking outside assistance (e.g. formal medical care). Before engaging in outside assistance, people may go through stages that include not noticing the condition, noticing the condition but not identifying it as a problem, identifying the condition as a problem but not having interest in addressing it, learning more about the condition, having interest in addressing the condition but not taking steps toward addressing it, exploring options for addressing the condition, and taking steps to address the condition. It is therefore valuable to provide resources (e.g. education and self-guided interventions) that can support people before they seek outside assistance, for example by guiding people through the steps leading up to seeking outside assistance.

Upon engaging with outside assistance, there are additional tools that become useful for maximizing the effectiveness of the assistance. For example, tools that can increase adherence to treatment, decrease appointment no-shows, and strengthen connections between care teams and the people they help. Such tools improve outcomes for the individuals receiving assistance, as well as benefiting the people and organizations providing the assistance.

Furthermore, receiving outside assistance from a single source is insufficient for many healthcare concerns. Instead, people must often engage with multiple organizations, resources, care providers, and other entities. These other organizations often extend beyond healthcare, to include entities such as social services organizations, educational institutions, and employers. People often have co-occurring concerns, thereby requiring assistance from multiple sources of outside assistance at the same time. Sometimes people will begin treatment at one facility, disengage from treatment, then begin treatment for the same condition at another facility. When people do complete treatment, they may wish to maintain an affiliation with the facility, for example as an "alumnus". Many healthcare concerns require attention and effort even after disengaging from outside assistance, making it important to continue to have access to resources regarding the condition.

Existing digital tools fail to address the real-world process of addressing healthcare concerns. There are applications that can be used before, during, and after treatment, but they don't interface with treatment providers to augment assistance. There are applications that interface with treatment providers and are accessible during and after treatment, but they're not usable before starting treatment and can only be connected to one treatment provider. There are applications that interface with treatment providers, are usable before, during, and after treatment, and can connect with multiple treatment providers, but they can only be connected to people (similar to a "friending" system in a social media application), not organizations or other entities. There are applications that consolidate medical records from multiple sources, but they don't connect to different types of organizations or provide functionality specific to the kind of outside assistance the user is receiving.

Accordingly, there is a need for an application system that allows a software application to be a source of support throughout the process of addressing healthcare concerns: providing support before, during, and after receiving outside assistance; augmenting the assistance received from any number of varied outside entities; continuing to provide support during the transition from one outside resource to another; allowing for different affiliations with the outside resource (e.g. "patient" vs. "alumnus"); and consolidating the assistance from multiple outside entities into a single tool.

SUMMARY OF THE INVENTION

Disclosed are systems, methods, devices, and non-transitory computer-readable storage media for establishing any number of connections between a user account and any number of general welfare entities. General welfare entities encompass any entity that may support the wellbeing of one or more individuals and/or communities, including but not limited to hospitals, social service organizations, schools, criminal justice systems, employers, healthcare facilities, groups of healthcare facilities, people, and medical devices. User accounts encompass any system and method (including but not limited to usernames and passwords, unique database identifiers, and/or device identifiers) of associating data with a specific individual. A user account can be connected to an entity to enable, for example, interaction with data associated with the user account and the connected entity, amended permissions associated with the user account and the connected entity, and/or updated features in software applications associated with the user account and the connected entity. The application system executing the connection may have specific rules that determine how the application system operates when any given connection is in place. For example, an individual may connect their user account to a healthcare clinic at which they're a patient, to access software application features that will support their treatment at the healthcare clinic and to provide the clinic with healthcare data the individual previously entered into the application. In another example, a healthcare clinician may connect their user account to a patient, to enable, for example, sending of text-based messages with the patient, access to remotely-captured health status data the patient has submitted between appointments, and modification of treatment plan data associated with the patient's user account. Furthermore, because a user account can be connected to an arbitrary number of entities, the patient in the first example may connect their account to a second (or third, or fourth, etc.) entity from which they receive support for their wellbeing; similarly, the clinician in the second example may connect their account to any number of patients.

Enabling any number of connections of user accounts to any number of entities allows users to first access an application's functionality (whether that functionality requires a user account or not), and later connect that account to any entities if needed. For example, an individual with a certain healthcare condition may begin using an application to learn more about the condition and to engage with features that guide the individual in taking preliminary steps towards addressing the condition. When that individual begins formal medical care, they are then able to connect their account to the organization providing medical care, as well as to clinicians at that organization, to facilitate treatment adherence and provide clinicians with information that can inform treatment decisions. Without this system, either the patient could use the application before treatment but not connect it to their treatment provider, or the patient could only access the application after starting treatment and couldn't receive help from the application beforehand.

Additionally, enabling any number of connections of user accounts to any number of entities allows individuals to use the same account and same application when interacting with multiple entities. For example, an individual could receive treatment for a healthcare condition at one organization and connect their account to that organization. Then, if they face another healthcare condition and receive treatment at a separate organization, the individual could connect their same account to the second organization. In one embodiment, different features may be activated within an application, based on the organization, type of treatment received, and other factors. Further, in another embodiment, depending on the features and the individual's privacy settings, the individual could send data to all connected organizations at once, or only send certain data to specific organizations. As a result, the individual can access a single account and application to receive multiple forms of health and wellness support. Without this system, the patient would have to use multiple applications and/or multiple accounts to receive digital support for all their healthcare concerns, resulting in duplicated effort and reduced adherence.

Additionally, enabling any number of connections of user accounts to any number of entities allows the disconnection of user accounts from entities when needed. For example, if an individual completes a treatment regimen from a healthcare organization and will no longer need to interact with the organization or engage in treatment activities, the individual can disconnect from the organization, which in some embodiments may end the bidirectional transmission of data with the organization and remove any features that were activated as a result of the connection. In other embodiments, some data and/or features may still be accessible and/or modifiable by one or all previously connected parties after a connection is removed. An individual is therefore able to retain control of data associated with their account regardless of which entities their account has been connected to or disconnected from.

In some embodiments, there may be any number of possible forms of connections between a user account and a specific type of entity. For example, there may be a data field associated with user accounts that defines the zero or more "roles" a user account is associated with. Exemplary roles include "patient", "clinician", and "administrator". If a user account is associated with both a "clinician" role and an "administrator" role, that user account may be connected to "Organization Type 1 Instance 1" as both a clinician and an administrator, forming two separate connections: a "clinician"-to-"Organization Type 1" connection, and an "administrator"-to-"Organization Type 1" connection. Each of those connections may result in different outcomes with regard to the application system(s) associated with the user account and connected entity, and in some embodiments an individual may be required to utilize distinct software applications to interact with each of the connections. As a result, an individual can use the same user account to perform multiple functions within an organization.

In some embodiments, an individual can modify data associated with their user account (e.g. "settings") to modify the outcomes of the connections established with their user account. For example, an individual may choose to prevent a specific organization (or multiple specific entities, or entities of a certain type) from accessing certain data associated with the user account that the organization would otherwise have been able to access. As a result, individuals have greater agency in determining how to best utilize connections to their user accounts.

In some embodiments, specific restrictions or rules may exist for how user accounts can be connected to entities. For example, a user account may be able to establish a limited number of a specific connection type, a user account may be able to connect with a specific organization in a limited number of roles, a user account may only establish a specific connection for a limited amount of time, and so forth.

In some embodiments, some user accounts may be able to interact with (e.g. create, view, modify, and remove) the connections of other user accounts. For example, an administrator user account may be able to create a connection between the user account of a patient and the user account of a clinician. For a user account to interact with the connections of other user accounts, it may be required that all user accounts have a connection to the same entity, and it may further be required that the way in which the user account is interacting with the connections of other user accounts is related to the entity to which all user accounts are connected. A first user account interacting with the connections of a second user account may not impact the ability of the second user account to interact with its own connections. In other embodiments, a user account cannot interact with the connections of other user accounts.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate embodiments and/or aspects of the disclosure and, together with the written description, serve to explain the principles of the disclosure. The accompanying drawings depict only exemplary embodiments of the disclosure and are not therefore to be considered to be limiting of its scope. Wherever possible, the same reference numbers are used throughout the drawings to refer to the same or like elements of an embodiment, and wherein:

FIG. 2 illustrates an exemplary embodiment of connecting user accounts to entities;

FIGS. 6A-F illustrate the different features that may be available within an application depending on the connection state(s) of the user account associated with the application;

DETAILED DESCRIPTION OF THE INVENTION

Figure 1:
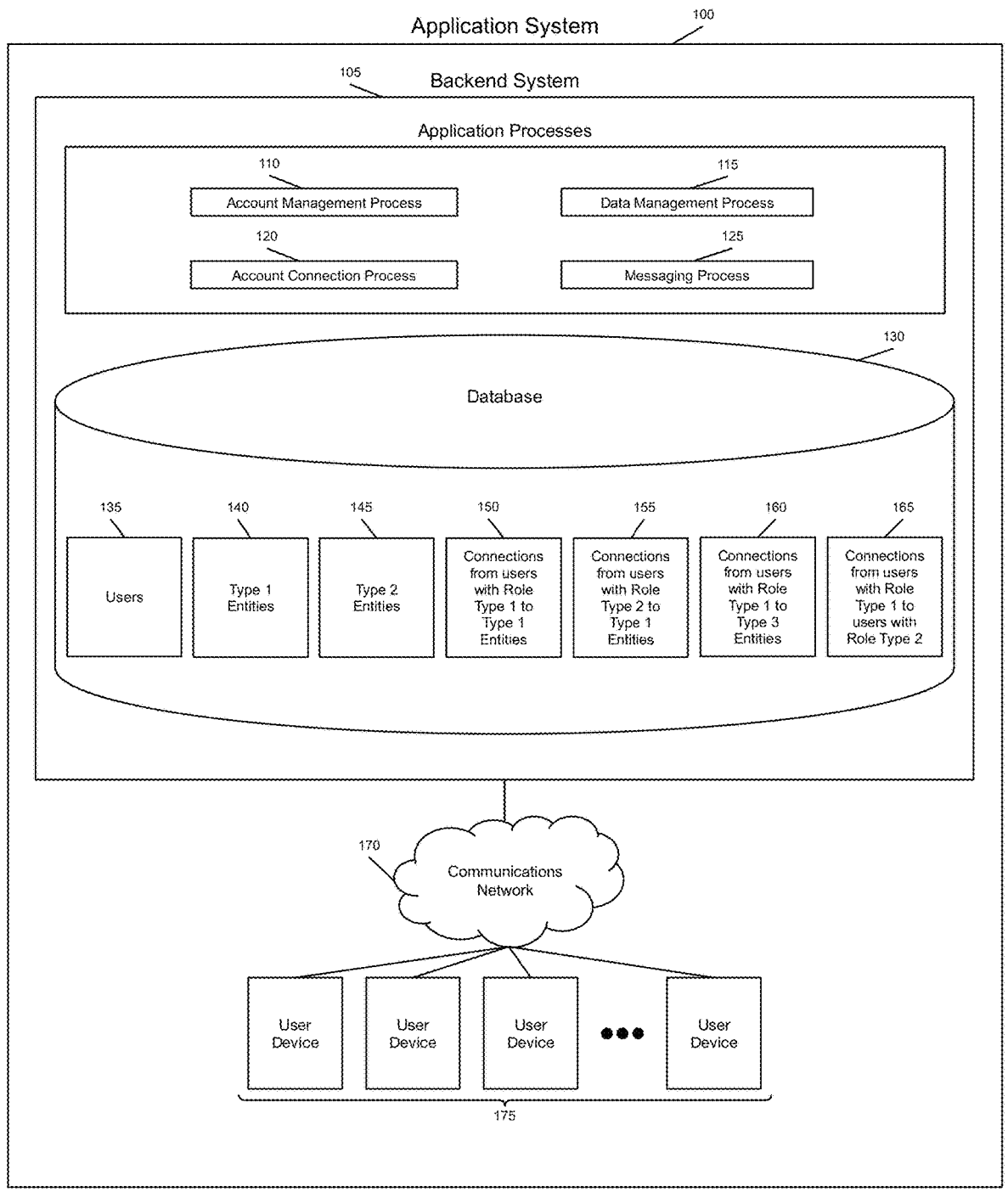
FIG. 1 illustrates an application system in accordance with an example embodiment of the disclosed invention.

Aspects of a system and method are provided for enabling any number of connections of user accounts to any number of entities. A user account can be connected to healthcare organizations, care team members, medical devices, and other entities to enable the individual associated with the user account to receive enhanced support for their wellbeing through a set of software applications that make use of the connection. For example, additional functionality can be available in a mobile app used by an individual with a user account connected to one or more healthcare organizations, and data transmission between the user account of that individual and the user accounts of the individual's care team could facilitate enhanced medical care for the individual.

Connecting user accounts enables interacting with multiple entities through a single user account and/or software application (or multiple software applications, if appropriate). As a result, data associated with a user account may continue to be associated with a user account regardless of which entities the user account is connected to and/or is disconnected from.

For example, an individual could have a behavioral healthcare condition. Before seeking formal treatment for the condition, the individual could download and use a mobile application, without creating an account, to learn more about the condition. Upon creating an account, the individual could access additional functionality in the mobile application. The individual may then decide to receive formal treatment at an outpatient clinic. The individual can connect their user account to the outpatient clinic (not connecting yet to any user accounts of the staff of the outpatient clinic), at which point the mobile application displays additional features to augment the treatment the individual receives from the outpatient clinic. Further, the administrators of the outpatient clinic gain certain permissions to interact with (e.g. access and modify) certain data associated with the individual's user account. In this example, the administrators can interact with this data because the administrator is using an account that has an "administrator" connection to the same outpatient clinic the individual is receiving care from. The administrator can create a connection between the user account of a clinician at the outpatient clinic and the user account of the individual receiving treatment. With this connection, the clinician has access to certain healthcare data the individual enters into their mobile application, and each party can send certain data to the user account of the other party.

That same individual could then require care for a second healthcare condition at a hospital. The individual could use the same mobile application and same user account to connect to the hospital, which is a different organization and different kind of organization than the outpatient clinic. Upon connecting the user account to the hospital, the mobile application displays additional features. Some of the features that were present in the app without any connections as well as some of the features that were present in the app upon connection to the outpatient clinic may also be utilized in the connection to the hospital. At the hospital, the individual connects their user account to multiple clinicians as well as to a medical device. With each connection, specific data operations and permissions are enabled. After being discharged from the hospital, the individual can disconnect their user account from the hospital. It may be the case that upon disconnecting from the hospital, all other connections associated with the user account's connection to the hospital (in this case, the clinicians and the medical device) are also disconnected. The individual's user account continues to be connected to the outpatient clinic, with relevant functionality and data operations persisting.

Later, the individual may no longer require treatment from the outpatient clinic. The individual can keep their user account connected to the outpatient clinic, or the individual (and/or an administrator) could disconnect the user account. Upon disconnecting the user account, the individual maintains access to the data associated with their account, and some functionality and data that were the result of the connection to the outpatient clinic may persist.

In the years following, the individual may become a clinician to treat the healthcare condition for which they received care at the outpatient clinic. The individual could use the same user account they utilized when receiving care as a patient, this time creating a clinician connection with the treatment clinic. If the individual worked as a clinician at multiple treatment clinics, they could create a clinician connection to each clinic. And if the individual rises to a leadership position at some of those clinics, the individual could form an administrator connection with those clinics as well.

FIG. 1 illustrates an application system 100 in accordance with an example embodiment of the disclosed invention. User devices 175 communicate with a backend system 105 to execute operations, including connecting a user account to another entity. Some operations may be possible without contact with a backend system. Many user devices 175 can communicate with the communications network 170 as well as with the backend system 105. The at least one user device 175 is configured to communicate with the at least one backend system 105 through the communications network 170. User devices 175 can use the communications network 170 and/or backend system 105 to send data to or otherwise interact with other user devices 175. Software applications can run on the user devices 175, communicating with the different elements of the application system 100.

Although the at least one user device 175 is shown as a single computing device, it is contemplated that the at least one user device 175 may include multiple computing devices, for example, in a cloud computing configuration. In addition, although the at least one backend system 105 is shown as a single unit, it is contemplated that the at least one backend system 105 may include multiple computing devices, for example, in a cloud computing configuration. The at least one backend system 105 may have an application or at least one component of an application, e.g., an account management process 110.

The communications network 170 can be the Internet, an intranet, or another wired or wireless communication network. For example, the communications network 170 may include a Mobile Communications (GSM) network, a code division multiple access (CDMA) network, 3rd Generation Partnership Project (GPP) network, an Internet Protocol (IP) network, a wireless application protocol (WAP) network, a WiFi network, a Bluetooth network, a satellite communications network, or an IEEE 802.11 standards network, as well as various communications thereof. Other conventional and/or later developed wired and wireless networks may also be used.

The at least one user device 175 includes at least one processor to process data and memory to store data. The processor processes communications, builds communications, retrieves data from memory, and stores data to memory. The processor and the memory are hardware. The memory may include volatile and/or non-volatile memory, e.g., a computer-readable storage medium such as a cache, random access memory (RAM), read only memory (ROM), flash memory, or other memory to store data and/or computer-readable executable instructions such as a portion or component of the application system 100. In addition, the at least one user device 175 further includes at least one communications interface to transmit and receive communications, messages, and/or signals.

The at least one backend system 105 includes at least one processor to process data and memory to store data. The processor processes communications, builds communications, retrieves data from memory, and stores data to memory. The processor and the memory are hardware. The memory may include volatile and/or non-volatile memory, e.g., a computer-readable storage medium such as a cache, random access memory (RAM), read only memory (ROM), flash memory, or other memory to store data and/or computer-readable executable instructions such as a portion or a component of the application system 100. In addition, the at least one system service further includes at least one communications interface to transmit and receive communications, messages, and/or signals.

The at least one user device 175 can be a laptop computer, a smartphone, a personal digital assistant, a tablet computer, a standard personal computer, or another processing device. The at least one user device 175 may include a display, such as a computer monitor, for displaying data and/or graphical user interfaces (GUIs). The at least one user device 175 may also include a Global Positioning System (GPS) hardware device for determining a particular location of the user device, an input device, such as a camera, a keyboard or a pointing device (e.g., a mouse, trackball, pen, or touch screen) to enter data into or interact with graphical and/or other types of user interfaces. In an exemplary embodiment, the display and the input device may be incorporated together as a touch screen of the smartphone or tablet computer.

The at least one user device 175 may display a GUI. The GUI may be provided by any one of the many applications interacting with the application system 100. The GUI enables a user of the at least one user device 175 to interact with the account connection system and execute tasks in support of general welfare.

The account connection system may be a component of an application and/or service executable by the at least one backend system 105 and/or application system 100. For example, the account connection system may be a single unit of deployable executable code or a plurality of units of deployable executable code.

The account connection system may also include a relational database management system (RDBMS) or another type of database management system such as a NoSQL database system that stores and communicates data from at least one database 130. The data stored in the at least one database 130 may be associated with a plurality of users associated with the application system 100. As an example, the database 130 may include one or more tables or data structures that may be organized to store the data. According to one aspect, the account connection system may take the form of one or more units of executable code running on a server that modifies and reads from one or more databases 130.

The database 130 of the backend system 105 may have one or more data structures (e.g. tables) for all users with an account associated with the application system 100. The data structure may have a field to store a unique identifier for the account, contact information, and other data. Every user account may have one or more roles associated with the user account ("patient", "clinician", "administrator", etc.), which may be used to determine the kinds of actions the user account can execute and the kind of data connections the user account can form. There may be all manner of data stored outside of the users database structure 135. In one embodiment, there are data structures for each of the entity types, and each instance of an entity may be associated with a unique identifier. For example, there may be one data structure for a specific kind of organization 140 in the database 130, and another data structure for a specific kind of device 145. Associating each instance of a specific entity type with a unique identifier may enable one approach of connecting a user account with entities of varied types.

The account connection system may be able to save data in the database 130, receive data from and send data to different endpoints, and perform actions on the data stored in the database 130. The data stored may relate to, for example, the healthcare information of the individuals who have user accounts in the application system 100, or other information about the entities associated with the application system 100. The data for any given user or entity may be accessed from different user devices 175, by transmitting the data through the communications network 170. This account connection system can connect to external computing devices having external software systems. The application system 100 can connect applications, modules, or components associated with it (such as the account connection system) to an external backend, through an application programming interface (API).

The application system 100 may manage the flow of data between the different kinds of applications. As an example, the application system 100 may have an internal application, module, or component that includes endpoints, backend actions, user roles, tokens, and a communications network. When a user takes an action (in any of the applications) that involves sending data to an internal or external application, module, or component, the data in a request may include an endpoint location, an action to perform at that endpoint (e.g. "POST", "PUT", "GET", or "DELETE"), an authentication token, and a data payload. In one example, the data payload may be formatted in JavaScript Object Notation (JSON) or another format. The data payload may include key-value pairs to identify the data that the application, module, or component is receiving, for example {title: "Example Title, description: "Example description"}. Microservices further enable the functionality of the application system 100, allowing data transfers between other computing systems.

The request may be sent over the communications network 170. The endpoint location and the action to perform informs the internal application, module, or component what category the action is and what specific action to take within that category, respectively. The authentication token allows the backend to determine if the user sending the request has the necessary permissions for taking the given action. The data payload, which may be empty in some cases, includes the data that the internal application, module, or component from the user uses to complete the requested action. The request also may utilize data not sent from the user but that is otherwise accessible to complete the action, it may use data from a combination of sources, or it may not utilize data at all. The application, module, or component would follow the specific, encoded rules associated with the request endpoint and action name to determine which data to access and how to use such data.

The application system 100 may have a security layer, microservices, a server, internal APIs, and connections with public APIs from other software systems. The security layer may include and/or interact with a user account creation system, which may allow for user authentication. When any user sends their login credentials to the application system 100, the application system 100 may verify that the credentials match a user account and then send a success response to the user device 175 sending the request. This success response may include an authentication token that allows the user to send authenticated requests from their logged-in user account.

The application system 100 can include an account management process 110 and data management process 115 to provide user account functionality and manage data relating to user accounts. The application system 100 may include any number of other processes or elements. The account management process 110, in coordination with the data management process 115 and/or other processes, may enable user account creation, login, logout, deletion, and updating of account information. The data management process 115, in coordination with the account management process 110, may allow users to save data to their account, for example data relating to their healthcare information. When a user logs in to their account and receives an authentication token, the user may be able to send requests to perform actions with the data associated with their account, for example downloading the data via the communications network 170 or modifying the data in the database 130. Other processes in the application system 100 may also work together with the account management process 110, the data management process 115, and other processes, for example a messaging process 125 for sending messages from one user account to another user account, or, for example, a notification process for sending alerts to user devices 175. Some processes and services may be outside of the application system 100.

The application system 100 may be able to connect a user account to other entities within or outside of the application system 100, including but not limited to other user accounts within the application system 100, organizations within the application system 100, and organizations outside of the application system 100. The application system 100 could achieve this connection by, for example, coordinating the account connection process 120 with the account management process 110 and the data management process 115. Each specific kind of connection may be defined by a set of operational rules for the application system 100. As a result of connecting a user account to another entity, the rules for handling data, functionality, and other elements of the application system 100 may be updated in accordance with the rules associated with the connection. For example: certain data from the user account and/or from the connected entity may be accessible by the other party; the user account and/or the connected entity may be able to modify data associated with the other party; the user account and/or the connected entity may be able to send data to the other party; services within the application system 100 relating to the user account and/or connected entity may be updated to reflect the connection; in software applications associated with the user account and/or connected entity, functionality may be added, removed, or updated. The operational changes that result from a connection may be altered by other factors, such as data associated with the user account and/or connected entity. The application system 100 may execute other commands to define, for example, which accounts have access to which data, from which users, and under which circumstances. There may be data transfer and other interactions between a user account and an entity without a connection existing between the two; the existence of a connection may modify the interactions between the two.

A user can connect their user account in this way to any number of entities, as long as the connection is supported by the application system 100. This connection would allow, for example, an individual to enter healthcare data into a mobile application before receiving treatment for the healthcare condition related to the healthcare data, then share that previously entered data with a healthcare provider once the individual initiates treatment. Further, because a user account can be connected to multiple entities, the person could receive treatment from a second healthcare provider for a second healthcare condition, and the rules for data transfer with the second healthcare provider may be different than for the first. Further, because the connection can be with entities of varied types, the person could connect their user account to healthcare clinicians, and also connect their user account to, for example, a hospital, for any data transfer beneficial for addressing their healthcare condition. Connections between user accounts and entities can be removed and updated as well.

To achieve a connection between a user account and an entity, the account connection process 120 may update data associated with the user account and/or the connected entity. One embodiment of the account connection process 120 could involve the presence of a data structure (e.g. a table) in the health application system 100 database 130 that records the unique identifiers of the user accounts and entities that have been connected in a specific way. For example, in this embodiment, there may be: a data structure for the connection between a user accounts and a first kind of treatment clinic, with the user account having the role of a patient 150; a separate data structure for the connection between a user account and a first kind of treatment clinic, with the user account having the role of a clinician 155; a separate data structure for the connection between a user account and a second kind of treatment clinic, with the user account having the role of a patient 160; a separate data structure for the connection between a user account and another user account, with the first user account having the role of a patient and the second user account having the role of a clinician 165; and so forth. Each of these exemplary data structures may contain, among other fields, fields for the unique identifier of the user account and the unique identifier of the connected entity.

Another embodiment of the account connection process 120 could involve updating fields in the data structure containing the user accounts. For example, in this embodiment, there may be a field for each of the different connection types in the data structure containing the user accounts, such as connecting the user account to a first kind of treatment clinic as a patient, connecting the user account to a first kind of treatment clinic as a clinician, connecting the user account to a second kind of treatment clinic as a patient, connecting the user account to another user account (the first user account as a patient, the second user account as a clinician), and so forth. In each of these fields, any number of unique identifiers for connected entities could be listed, indicating the entities with which the user account has established the given connection. A further embodiment may involve modification of data in the data structure associated with the connected entity. There may be any number of other embodiments to create, remove, update, or otherwise modify connections with user accounts, and there may be any number of other implementations of the embodiments listed herein. For example, there could be many connections made at once.

The account management process 110 and/or other processes can then use the data about any connections associated with a user account to modify the behavior of the application system 100 with regard to the given user account, connected entity, and/or other entities. In some embodiments, the account connection process 120, data management process 115, and/or other processes can be configured to define specific rules for specific forms of account connections.

In some embodiments, there may be software applications accessible on user devices 175, with GUIs for interacting with the account connection system. Users, who may need to be logged in to perform such actions, may be able to create connections with other entities, request connections with other entities, accept requests for connections with other entities, remove connections with other entities, create connections between other user accounts and other entities, remove connections between other user accounts and other entities, and perform other actions relating to connecting user accounts with entities.

The user account connection system may enable additional functionality in applications running on user devices 175. Applications may include mobile apps, applications running in a browser, applications downloaded to a desktop computer storage system, or other executable programs. The functionality in these applications may interact with the application system 100, the backend system 105, and/or other external systems. For example, the user can enter data about their health status into the application, which then is transmitted to the backend system 105 through the communications network 170. The backend system 105 can determine the actions it performs with that data, based on the request the data was transmitted with. For example, that data may be saved in the database 130 entry for the user, it may also be sent to entities connected to the user's account, it may be sent to entities connected with the user's account without being saved in the database 130, or it may be handled in other manners.

Some applications may only be accessible to users that have a specific role associated with their user account. For example, a user with only the "patient" role may not be able to log into an application that requires a "clinician" role. In another example, a user with both "patient" and "clinician" roles may be able to log into both an application that requires a "patient" role as well as an application that requires a "clinician" role. Some applications may be accessible to users with any role or no role, and some applications may not require a login at all.

FIG. 2 illustrates an exemplary embodiment of connecting user accounts to entities.

FIG. 2 illustrates three account connections: account connection 205, account connection 210, and account connection 215. As shown, each account connection includes fields for an index, an account identifier, an entity identifier, and a connection status.

The index field can include a unique record index that uniquely identifies the connection record in the data structure. As shown, the unique index for account connection 205 is 1, the unique index for account connection 210 is 2, and the unique index for account connection 215 is 3.

The account identifier field can include data identifying the user account that has been connected with an entity. As shown, the user account with the identifier 31 is the user account involved in both account connection 205 and account connection 210. The user account with the identifier 87 is the user account involved in account connection 215.

The entity identifier field can include data identifying the entity connected with the user account. As shown, for account connection 205 the user account with the identifier 31 is connected to the entity with the identifier 45, for account connection 210 the user account with the identifier 31 is connected to the entity with the identifier 6, and for account connection 215 the user account with the identifier 87 is connected to the entity with the identifier 307. In this example, the user account 31 is connected to two entities, and the user account 87 is connected to one entity. As a result of these connections, the operations of any associated application systems may be modified with regard to the one or more relevant user accounts, connected entities, and/or other entities.

The connection status field can include data identifying the current status of the connection between the user account and the connected entity. As shown, for account connection 205 the connection status is "accepted", for account connection 210 the connection status is "pending", and for connection status 215 the connection status is "canceled". The data in the connection status field may modify the outcome of a connection: the same user account may have two of the same kind of connections to two entities of the same type, but the connection may differ based on the connection status. There may be other values possible in the connection status field, beyond those shown in FIG. 2. Further, in some embodiments there may not be a connection status field, in which case when the same user account has two of the same kind of connections to two entities of the same type, then the connection may not differ. Further, in some embodiments there may be any number of fields that modify the outcome of a connection.

Although listing account connections in a data structure for each specific form of a connection is used as one example of how user accounts can be connected to other entities, this is only one possible embodiment and is not meant to be limiting. Connecting user accounts to an arbitrary number of other entities can be performed in any of numerous ways known in the art.

Figure 3A:
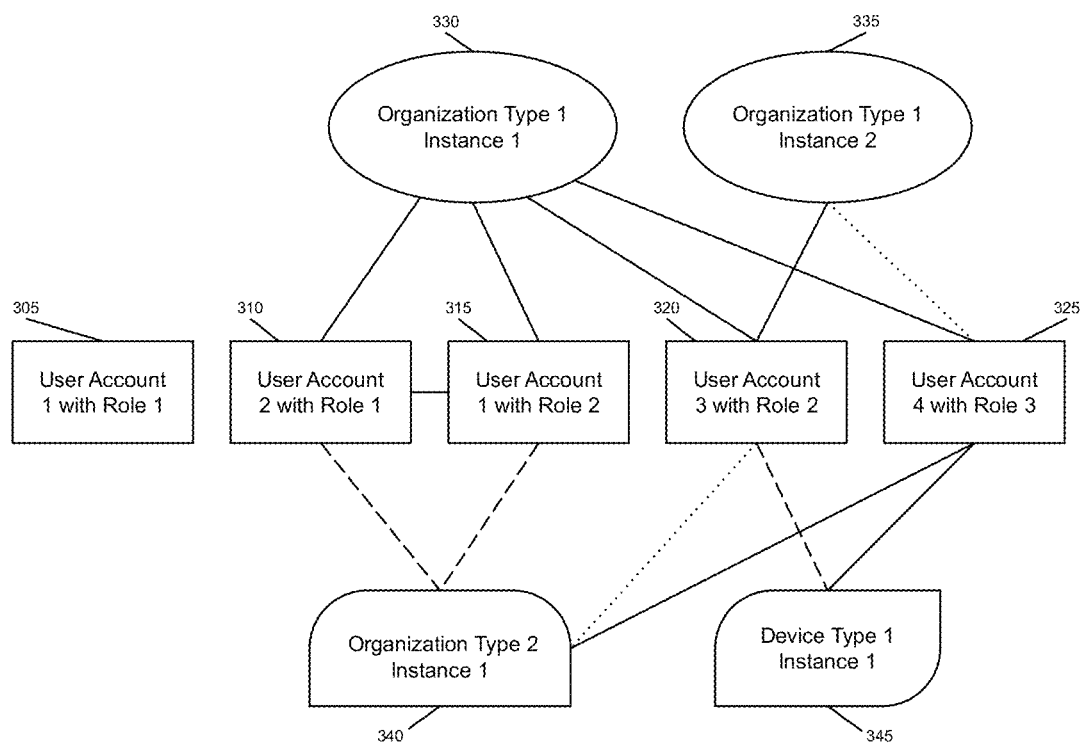
FIGS. 3A-B illustrate exemplary user account connection states.
Figure 3B:
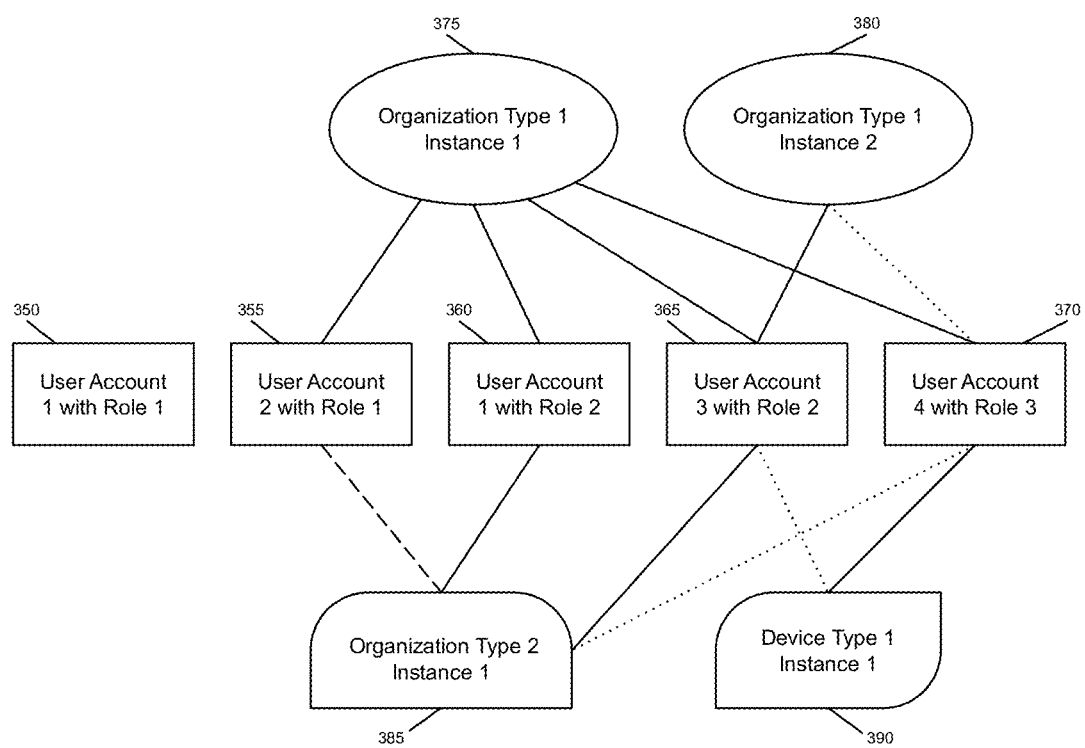

FIG. 3A-B illustrate exemplary user account connection states.

The exemplary states in FIG. 3A are 305, 310, 315, 320, and 325. Connection state 305 represents a user account that hasn't established any "Role 1" connections. Connection state 310 represents a user account that has a "User Account Role 1"-to-"User Account Role 2" approved (shown by a solid line) connection, a "User Account Role 1"-to-"Organization Type 1" approved connection, and a "User Account Role 1"-to-"Organization Type 2" pending (shown by a dashed line) connection. Connection state 315 represents a user account that has a "User Account Role 2"-to-"User Account Role 1" approved connection, a "User Account Role 2"-to-"Organization Type 1" approved connection, and a "User Account Role 2"-to-"Organization Type 2" pending connection. It should be noted how the user account in connection state 305 is the same user account as connection state 315, but the connection is different because it incorporates a different characteristic (in this example, a different "role" value) of the user account. In some embodiments, it may be required that before a user account can establish a specific connection with a specific entity, both the user account and the specific entity must both be connected to the same third entity (or any number of other entities). In other embodiments, such a requirement may not exist. Connection state 320 represents a user account that has two "User Account Role 2"-to-"Organization Type 1" approved connections—one to Organization Type 1 Instance 1 and the other to Organization Type 1 Instance 2—as well as a "User Account Role 2"-to-"Organization Type 2" canceled (shown by a dotted line) connection and a "User Account Role 2"-to-"Device Type 1" pending connection. Connection state 325 represents a user account that has a "User Account Role 3"-to-"Organization Type 1" approved connection, a "User Account Role 3"-to-"Organization Type 1" canceled connection, a "User Account Role 3"-to-"Organization Type 2" approved connection, and a "User Account Role 3"-to-"Device Type 1" approved connection. In some embodiments, although the user accounts for connection states 320 and 325 are not connected to each other, there may be data interactions and/or other manners of interactions between them, because both user accounts are connected to the same entity.

FIG. 3B shows possible examples (350, 355, 360, 365, and 370) of how the user account connection states shown in FIG. 3A could change over time. In connection states 355 and 360, the "User Account Role 1"-to-"User Account Role 2" approved connection from connection states 315 and 320 has been removed, however the approved connections to Organization Type 1 Instance 1 remains. Also in connection state 360, the "User Account Role 2"-to-"Organization Type 2" pending connection has become an approved connection, signifying that a full connection has been established. In connection state 365, the "User Account Role 2"-to-"Organization Type 2" canceled connection from connection state 320 is now an approved "User Account Role 2"-to-"Organization Type 2" connection, and the "User Account Role 2"-to-"Device Type 1" pending connection is now a "User Account Role 2"-to-"Device Type 1" canceled connection. In connection state 370, the "User Account Role 3"-to-"Organization Type 2" approved connection from connection state 325 is now a "User Account Role 3"-to-"Organization Type 2" canceled connection.

In any given embodiment of a connection, the exact result of the connection—in terms of data transfer, data modifications, feature updates, functionality modifications, application modifications, service updates, and other changes—will depend on the nature of the at least one user account, the at least one connected entity, and the at least one specific connection established. The connection may only be relevant when the user is logged in to certain applications, having no impact when the user is logged in to other applications. Further, the connection may determine which applications the user can log in to. Beyond "approved", "pending", and "canceled", there may be other states that a connection can be in. Alternatively, connections may not have any such modifiers, and be simply connected or not connected. Further, connections may exist with "roles" for the at least one user account, or there may be other modifiers regarding the at least one user account and/or at least one connected entity, or there may be no such modifiers.

In some embodiments, for example if a user account has a certain role associated with it, a user account may establish connections for other user accounts. There may be specific situations in which a user account can establish connections for other user accounts, for example if the first user account is itself connected to the user account for which it's establishing a connection, or if the first user account is connected to the same entity as the user account for which it's establishing a connection. User accounts with certain permissions may designate other user accounts to have the same or other permissions. User accounts may have other characteristics that enable further functionality relating to user account connections.

In some embodiments, there may be rules regarding certain connections, such as maintaining a limit on the number connections of a certain form a user account can establish, maintaining a limit on the number of user accounts that can establish a certain form of connection to an entity, or other such limitations. In other embodiments, there may be no such rules.

Figure 4:
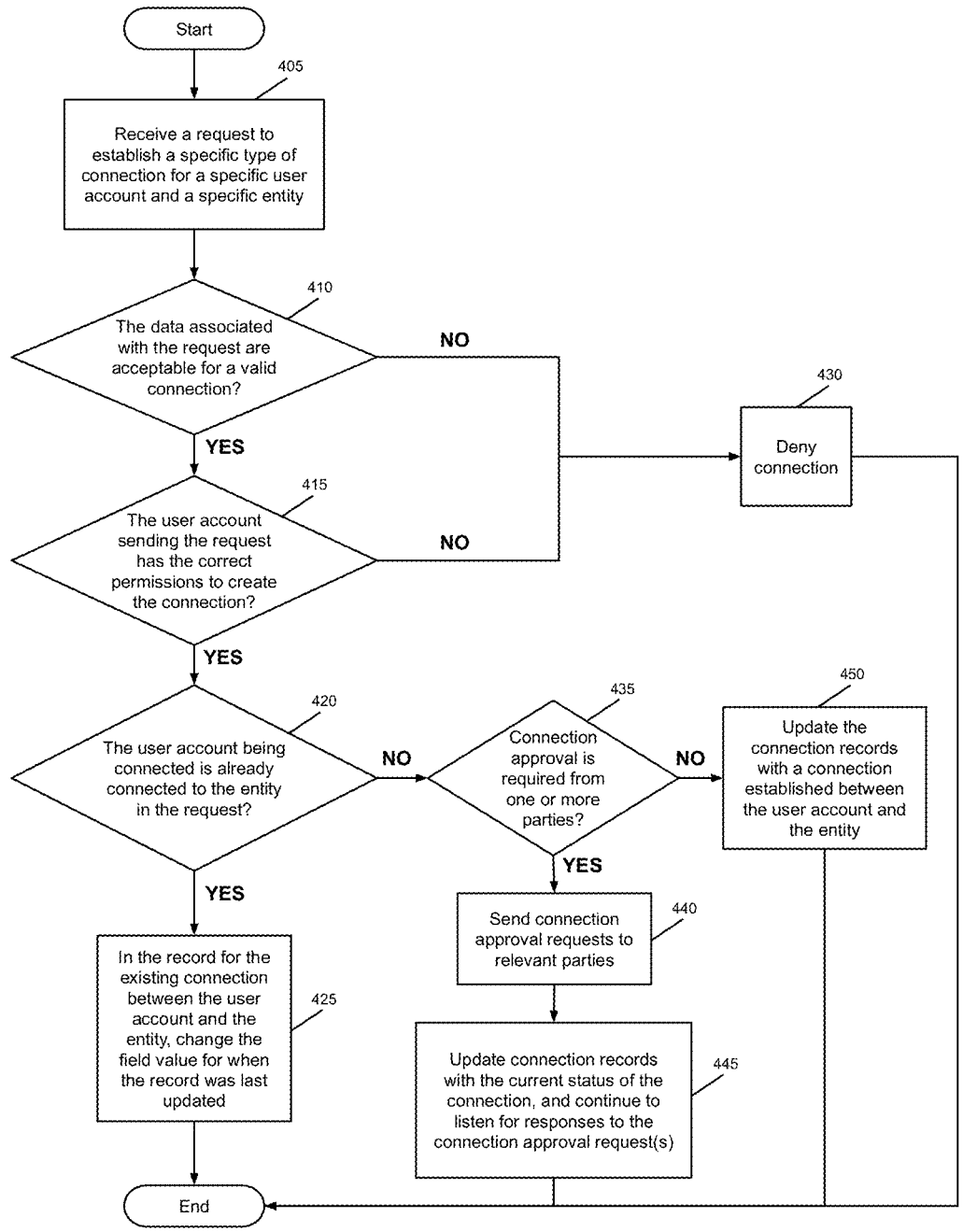
FIG. 4 illustrates an exemplary method embodiment of connecting a user account to an entity.

FIG. 4 illustrates an exemplary method embodiment of connecting a user account to an entity. Although specific steps are shown in FIG. 4, in other embodiments a method can have more, fewer, and/or different steps. As shown, the method begins at block 405 where a request to establish a specific connection for a specific user account and a specific entity is received.

At block 410 it is determined whether the data associated with the request are acceptable for a valid connection. If at block 410 it is determined that the data associated with the request are not acceptable for a valid connection, the method continues to block 430 where the request to connect the user account to the entity is denied and the method ends. However, if at block 410 it is determined that the data associated with the request are acceptable for a valid connection, the method continues to block 415 where it is determined whether the user account sending the request has the correct permissions to create the connection.

If at block 415 it is determined that the user account sending the request does not have the correct permissions to create the connection, the method continues to block 430 where the request to connect the user account to the entity is denied and the method ends. However, if at block 415 it is determined that the user account sending the request does have the correct permissions to create the connection, the method continues to block 420 where it is determined whether the user account is already connected to the specified entity in the specified role.

If at block 420 it is determined that the user account has already been connected to the specified entity in the specified role, then the record for the existing connection can be updated to change the field value for when the record was last updated and the method ends. However, if at block 420 it is determined that the user account has not already been connected to the specified entity in the specified role, then the method continues to block 435 where it is determined whether the connection must be approved by one or more parties involved in the connection.

If at block 435 it is determined that the connection does not require approval from one or more parties involved in the connection, then the connection of the user account in the specified role with the specified entity is established and the method ends. However, if at block 435 it is determined that the connection does require approval from one or more parties involved in the connection, then a connection approval request is sent to the relevant parties. Then the connection records are updated with the status of the connection, and the method continues to listen for response(s) to the connection approval request(s). The method then ends.

Figure 5:
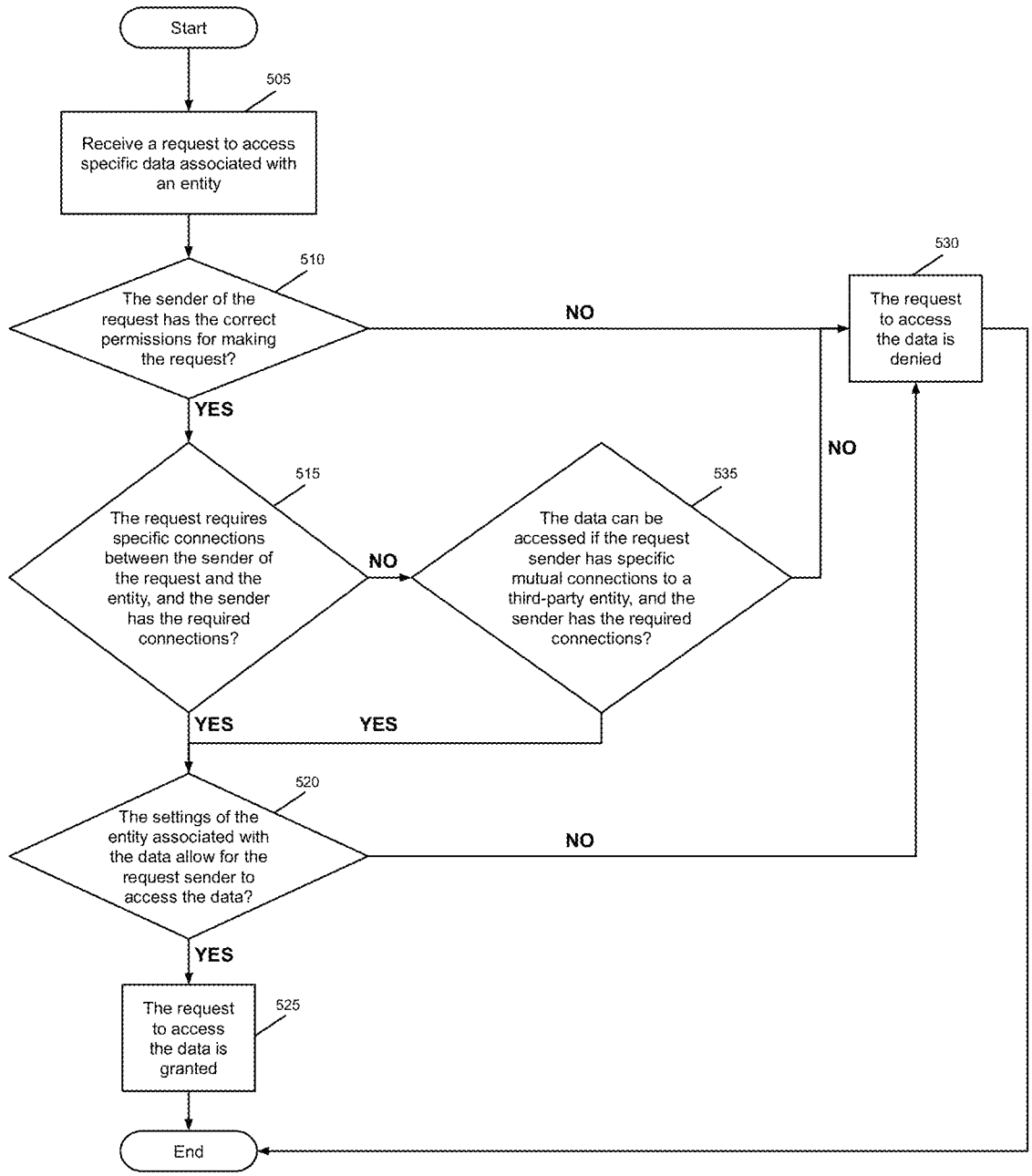
FIG. 5 illustrates an exemplary method embodiment of accessing data associated with an entity.

FIG. 5 illustrates an exemplary method embodiment of accessing data associated with an entity. Although specific steps are shown in FIG. 5, in other embodiments a method can have more, fewer, and/or different steps. In another embodiment, steps similar to those shown in FIG. 5 could represent a method of handling the modification of data, or handling other interactions with data. As shown, the method begins at block 505 where a request to access specific data (e.g. healthcare information) for a specific entity (e.g. a user account) is received.

At block 510 it is determined whether the sender of the request has the correct permissions to make the request. If at block 510 it is determined that the sender of the request does not have the correct permissions, the method continues to block 530 where the request to access the data is denied and the method ends. However, if at block 510 it is determined that the sender of the request has the correct permissions, the method continues to block 515 where it is determined whether the request requires specific connections between the sender of the request and the entity the requested data is associated with and whether the sender has the required connections.

If at block 515 it is determined that the sender of the request does not have the required connections, the method continues to block 535 where it is determined whether the requested data can be accessed if the sender of the request has a specific kind of mutual connection to a third-party entity and whether the request sender has the required connection. However, if at block 515 it is determined that the sender of the request has the required connections, the method continues to block 520 where it is determined whether the settings of the entity associated with the requested data allow the sender of the request to access the data.

If at block 535 it is determined that the sender of the request lacks any necessary mutual connections, the method continues to block 530 where the request to access the data is denied and the method ends. However, if at block 535 it is determined that the sender of the request has the required mutual connections, the method continues to block 520 where it is determined whether the settings of the entity associated with the requested data allow the sender of the request to access the data.

If at block 515 or block 520 it is determined that the settings of the entity associated with the requested data do not allow the sender of the request to access the data, the method continues to block 530 where the request to access the data is denied and the method ends. However, if at block 515 or block 520 it is determined that the settings of the entity allow the sender to access the data, the method continues to block 525 where the request to access the data is granted and the method ends.

FIGS. 6A-F illustrate the different features that may be available within an application depending on the connection state(s) of the user account associated with the application.

FIG. 6A illustrates an application state 605 that has no user account associated with it. Although no user is logged in, the application may still offer zero or more features (Feature 1 in the figure) to a user of the application. The application may save data to the user device the application is running on. Although the application is not connected to a user account, the application may still send and receive data from the application system and/or other systems over a communications network.

FIG. 6B illustrates an application state 610 that has a user account associated with it (e.g. a user is logged in to the application), in this case User Account 1, but the user account is not connected to any entities. With a user logged in to the application, zero or more additional features (Feature 2 in the figure) may be available within the application. Further, any features that were available without a user account being associated with an application (e.g. Feature 1) may have additional functionality with the association of a user account.

FIG. 6C illustrates an application state 615 that has a user account associated with it, and the user account is connected to an entity (Organization 1 635 in the figure). With a connection to an entity, zero or more additional features (Feature 3 in the figure) may be available within the application. The application may require that the user is logged in to their user account to access features that result from the connection of one or more entities, or it may not. The zero or more additional features may specifically relate to the connected entity, or they may not. Further, any features that were available without a user account and/or without the user account connected to the entity (e.g. Feature 1 and Feature 2) may have additional functionality with the connection to an entity.

FIG. 6D illustrates an application state 620 that has a user account associated with it, and the user account is connected to two entities (Organization 1 635 and Organization 2 640 in the figure). With a connection to multiple entities, zero or more additional features (Feature 4 in the figure) may be available within the application. Further, features that were activated as a result of a previous connection to an entity (Organization 1 635 in the figure) may receive additional functionality relating to the newly connected entity (Organization 2 640 in the figure).

FIG. 6E illustrates an application state 625 that has a user account associated with it, and the user account has disconnected from an entity it was previously connected to (Organization 1 635 in the figure) while maintaining its connection with another entity (Organization 2 640 in the figure). Upon removing a connection to an entity, the features that were previously activated as a result of the connection to that entity may no longer be accessible within the application. In other cases, for example if the user account maintains a connection with a separate entity and that connection activates the same features as the disconnected entity, then some or all of the features may continue to be accessible. If all features continue to be accessible, the features that were originally activated as a result of a connection to the now-disconnected entity may no longer have functionality relating to the now-disconnected entity, as seen in Feature 3.

FIG. 6F illustrates an application state 630 that has a user account associated with it, and the user account has disconnected from all entities it was previously connected to. Upon disconnecting from all entities, one or more features that were activated by a connection to that entity may still be available within the application (Feature 4 in the figure), however the one or more features may no longer have functionality relating to the now-disconnected entities.

These illustrations refer to "features" as the manifestation of changes that result from connecting a user account to one or more entities, however a change in "features" is used only as an example. The operations of an application may change in any number of ways as a result of connecting or disconnecting a user account to or from entities.

In one embodiment, the application can store in the memory of a user device the instructions for how the application should operate based on all possible connections a user account can establish. The application could receive, via a communications network, the connections a user account is associated with as well as data about those connections, and then use the stored instructions to operate in accordance with those connections, for example by displaying specific features in the GUI. This implementation is one example of many possible embodiments.

FIGS. 7A-H illustrate an exemplary application 700 that interacts with the user account connection system, specifically, an "Administrator Application" for a healthcare organization.

Figure 7A:
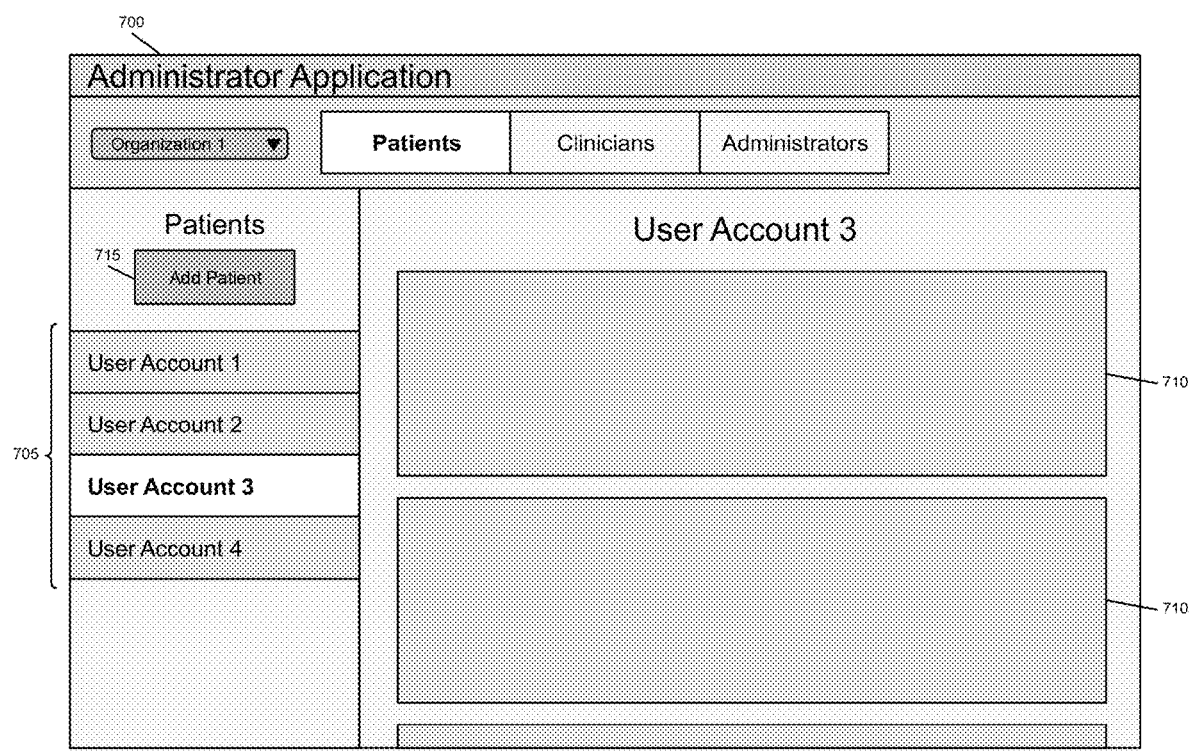
FIGS. 7A-H illustrate an exemplary application that interacts with the user account connection system.

FIG. 7A illustrates the "Patients" page of the exemplary Administrator Application 700. A user may need to be logged in to a user account with an "administrator" role for an organization (Organization 1 in the figure) to access the application. The Patients page displays a list of user accounts 705 connected in a "patient" role to the healthcare organization the Administrator Application 700 is interfacing with (Organization 1 in the figure). The patients may be displayed in the list by accessing data associated with their user account, such as their first and last name. Upon selecting a patient (User Account 3 is selected in the figure) the administrator may interact with features 710, which may include accessing certain data associated with the selected patient's user account, modifying data associated with the selected patient's user account, modifying data about the organization with which the Administrator Application 700 is interfacing, and other interactions. The administrator can select "Add Patient" 715 to view a GUI for starting the process in which the user account, in the role of "patient", is connected to the healthcare organization.

It should be noted that a first user account (e.g. the user account of the administrator using the Administrator Application 700) may not have to be connected to a second user account to interact with certain data associated with the second user account (e.g. accessing the first and last name associated with the user account). In some embodiments, a first user account may have to have specific permissions (e.g. through a specific "role" associated with the first user account) to interact with certain data associated with a second user account it lacks a connection with. In other embodiments, there may be an additional or exclusive requirement that the first user account and the second user account each have a connection to the same entity (e.g. a specific healthcare organization) for the first user account to be able to interact with certain data associated with the second user account.

Figure 7B:
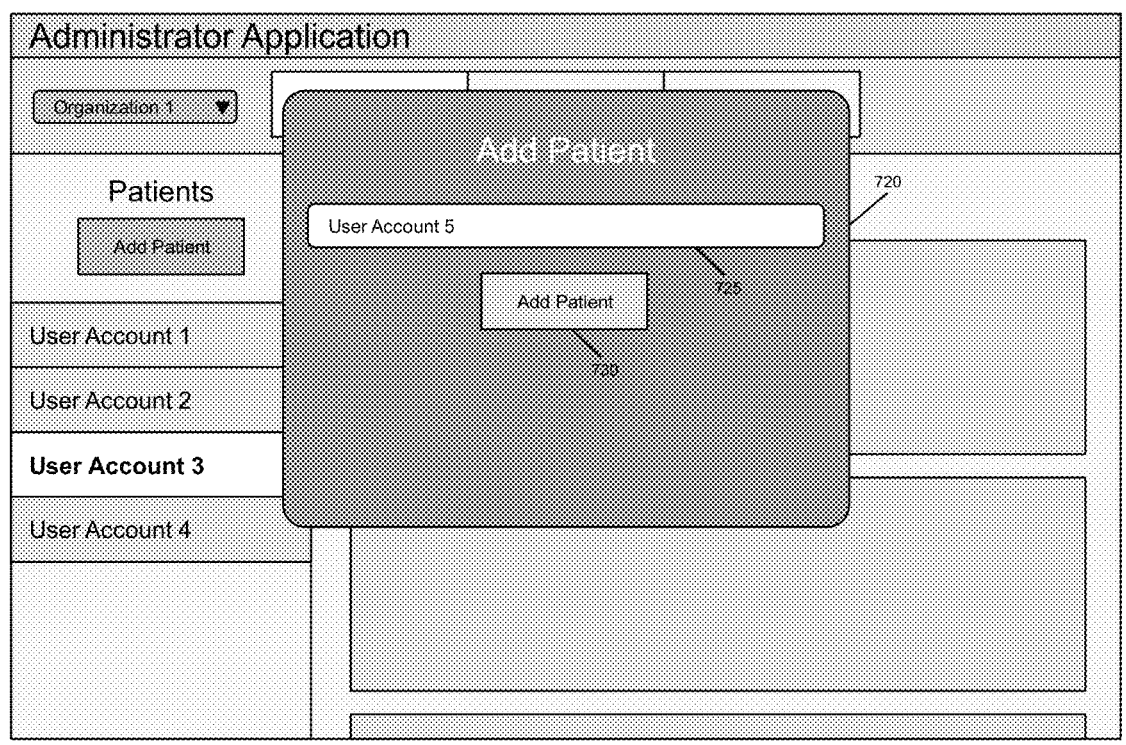

FIG. 7B illustrates an exemplary GUI for establishing a connection between a user account and an organization. The GUI contains a form 720 with a field 725 for entering unique identifying information about the desired user account. Upon entering identifying information about the desired user account, the administrator can select "Add Patient" 730 to establish a connection between the user account, in the role of "patient", and the healthcare organization.

There are many other possible embodiments of this GUI. For example, the form may have fields (e.g. first and last name) that don't uniquely identify the desired user account, combined with an option to "Search" among possible user accounts. Upon selecting "Search", the zero or more user accounts that match the search criteria can be displayed to the administrator, along with additional identifying information that would allow the administrator to add the correct user account. A further embodiment may include a confirmation step, in which, after choosing to add a given user account, a GUI window is displayed that requires the administrator to either confirm that they would like to add the user account they selected, or cancel adding the selected user account. It should be further noted that the administrator is modifying the connections of a user account to which they're not logged in and may not have ownership over. In some embodiments, a first user account must be connected to the same entity as a second user account for the first user account to be able to modify the connections of the second user account. In other embodiments, no such requirement exists. Further, in some embodiments a user account may modify its own connections with entities, without requiring the actions of a third-party user account as shown in this illustration. Further, in some embodiments a user account may send a connection request to an entity, which must be approved by a different user account associated with the entity. Further, in some embodiments the specific type of connection may dictate whether a first user account can modify the connections of a second user account, whether a user account can modify its own connections, and/or whether one or more other connection modification permissions exist.

Figure 7C:
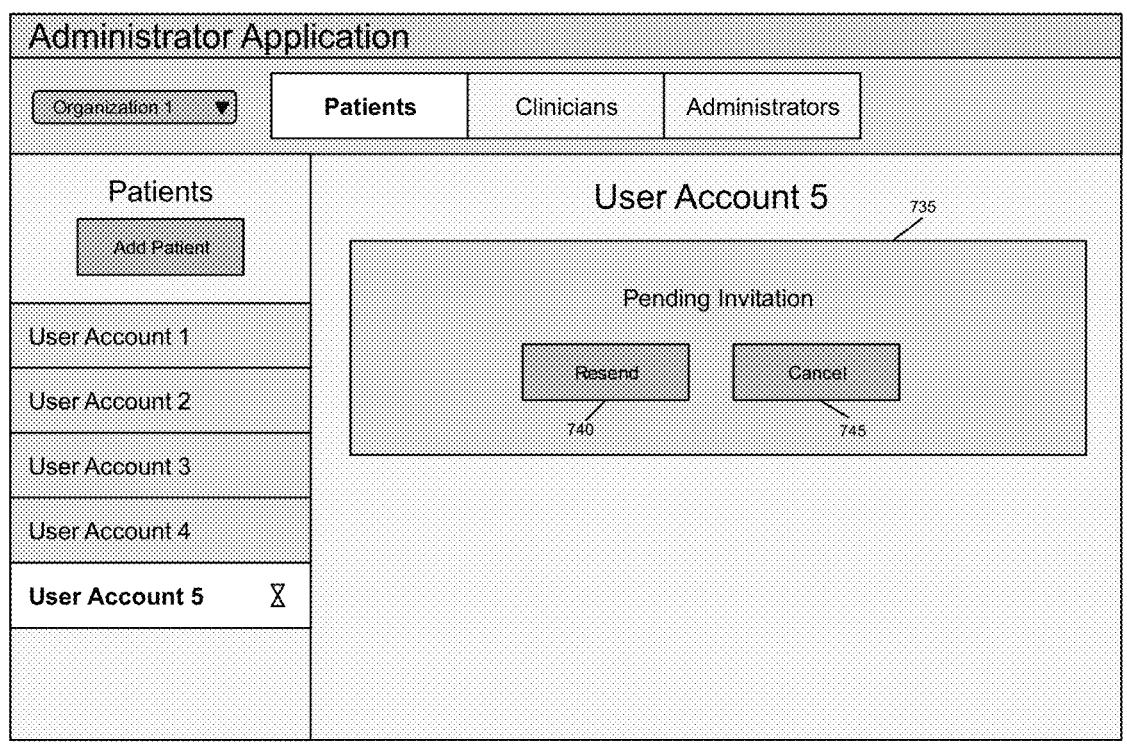

FIG. 7C illustrates an exemplary view of the Administrator Application 700 after a connection to a user account has been initiated. In this view, a pending connection has been established, resulting in limited interactions between the organization and the desired user account. For example, instead of the features that are available for patients with an approved connection, for patients with a pending connection, administrators may only be able to view that they've sent the connection request 735, resend the connection request 740, or cancel the connection request 745. However, certain kinds of connections may not require approval and instead be fully established with a single request.

Figure 7D:
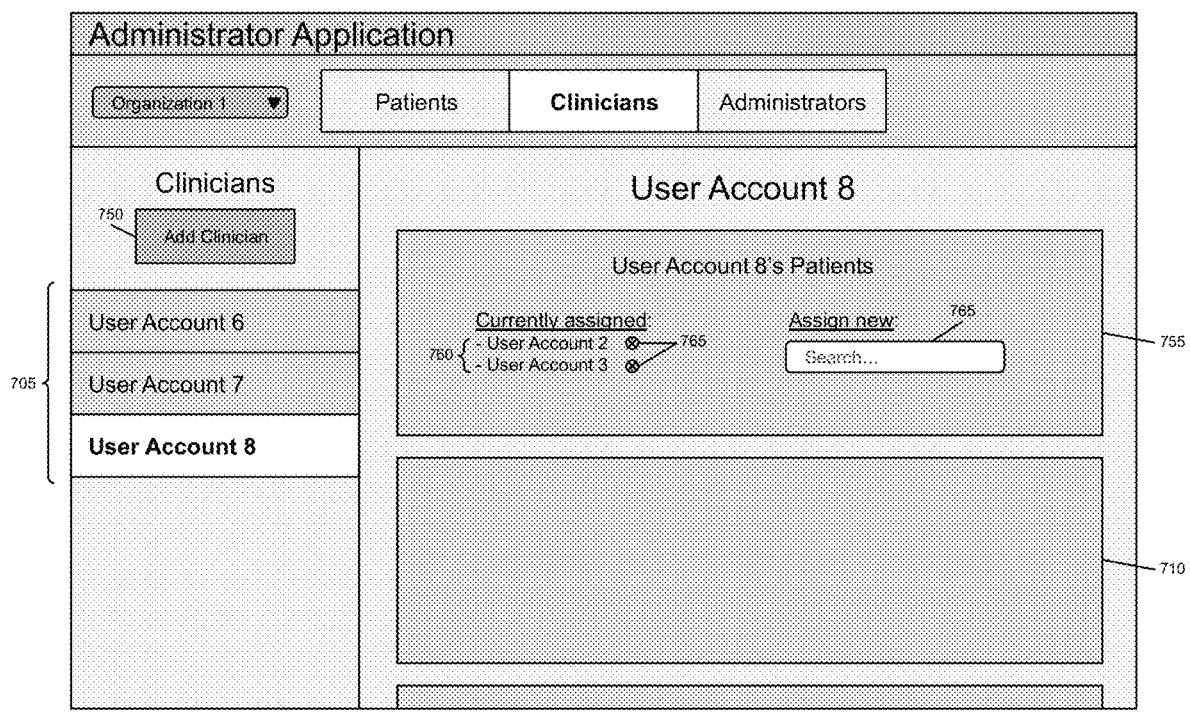

FIG. 7D illustrates the "Clinicians" page of the exemplary Administrator Application 700. In this exemplary application, the GUI for the Clinicians page is similar to that of the Patients page illustrated in FIG. 7A (i.e. having a list of user accounts that have the relevant connection to the organization 705, features for interacting with those user accounts 710, and the ability to connect a new user account to the organization in the "clinician" role 750), however GUIs for different forms of connections with a given organization need not resemble each other and may have any appearance and functionality. In this exemplary GUI, for example, there is a section for managing the list of patients a clinician treats 755. In this illustration, the section includes identifiers of the patients a clinician treats 760, GUI elements for removing the user accounts as patients of the clinician 765, and a GUI element for adding additional user accounts as patients of the clinician 770. As a result, the user of this Administrator Application 700 is able to create, remove, and otherwise modify the connection between one user account in the role of "patient" and a second user account in the role of "clinician". In some embodiments, a user account must be connected to the same entity as all user accounts that it requests to modify. Further, in some embodiments a user account must have specific permissions (e.g. through a specific "role" associated with the user account) to modify the connections of multiple user accounts. In other embodiments, no such requirements exist.

Figure 7E:
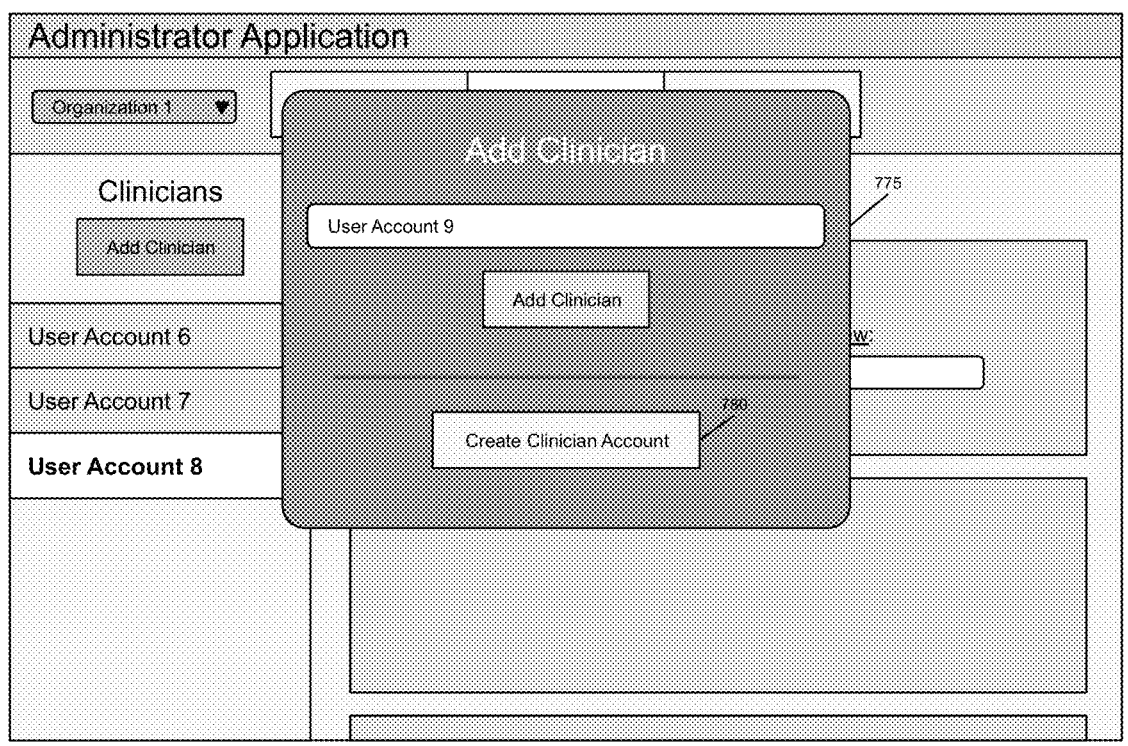

FIG. 7E illustrates an exemplary GUI for establishing a connection between a user account and an organization 775. The GUI is similar to the one illustrated in FIG. 7B. However, in this GUI, there is the additional GUI element "Create Clinician Account" 780. This GUI element provides the ability to create a new user account, such that upon the creation of the user account, the newly created user account immediately has a "clinician" connection established with the organization. GUIs for establishing user account connections need not resemble other GUIs for user account connections that are within the same application or other applications and can have any appearance and functionality.

Figure 7F:
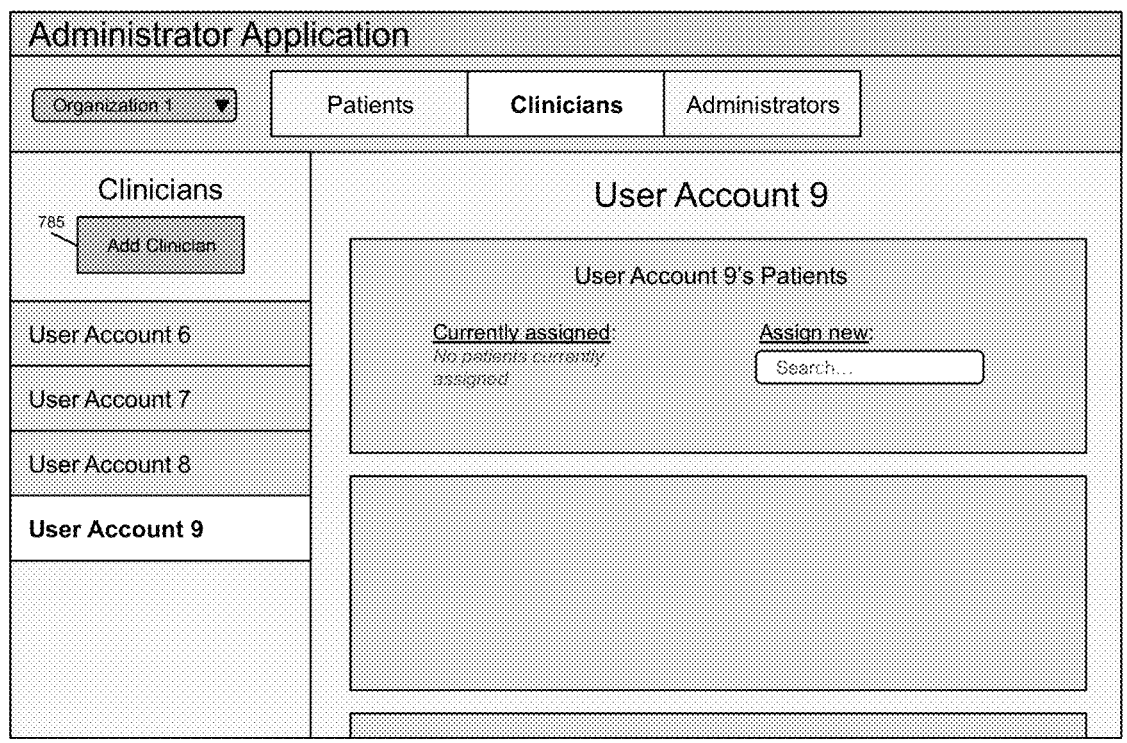

FIG. 7F illustrates an exemplary view of the Administrator Application 700 after a connection to a user account has been established. In this view, the connection with User Account 9 in the role "clinician" has been established immediately after the administrator using the Administrator Application 700 sent a user account connection request, with no need for approval from any party. User Account 9 is fully connected to the organization in the "clinician" role.

Figure 7G:
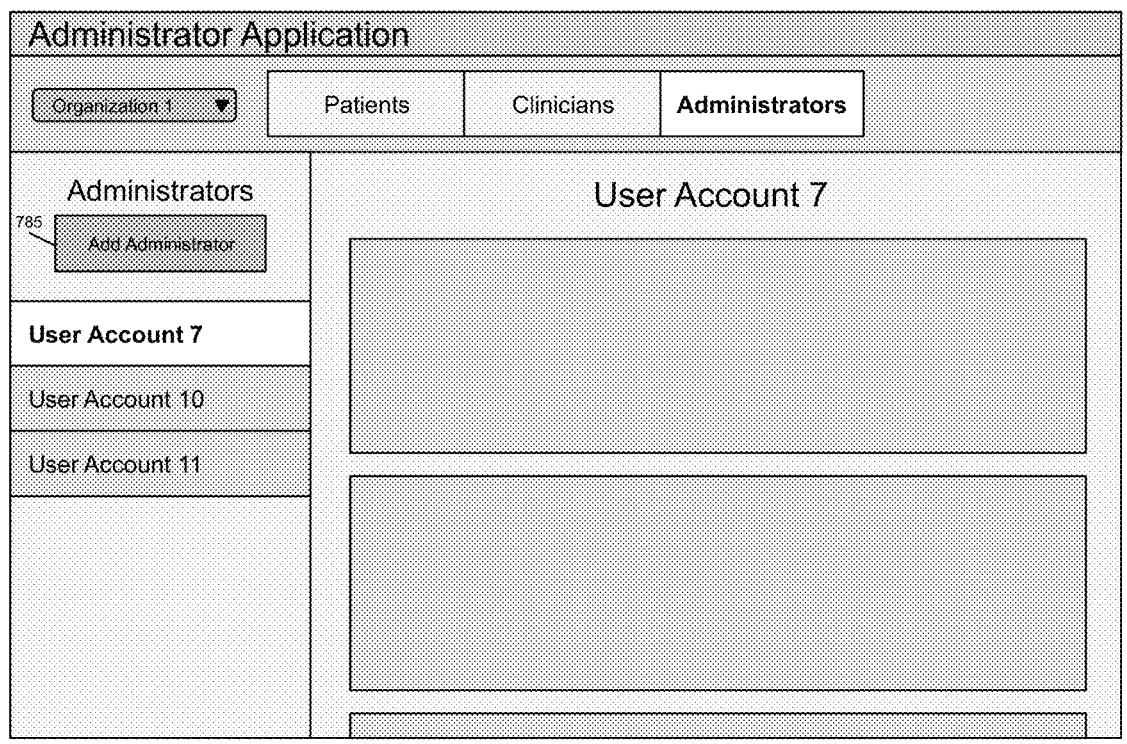

FIG. 7G illustrates the "Administrators" page of the exemplary Administrator Application 700. In this exemplary application, the GUI for the Administrators page is similar to that of the Patients page illustrated in FIG. 7A and the Clinicians page in FIG. 7D. This exemplary Administrator Application 700 offers the ability to establish a connection between the organization and a user account in the role of "administrator" 785, and the GUI for creating that connection may or may not be similar to the GUI for establishing "patient" connections 720 (shown in FIG. 7B) and/or the GUI for establishing "clinician" connections 775 (shown in FIG. 7E). It should be noted that User Account 7 is listed in both the Clinicians page and the Administrators page, indicating that User Account 7 has at least two connections to the organization, one in the "clinician" role and another in the "administrator" role. When creating multiple connections for a single user account (whether in multiple "roles", to multiple organizations, or other forms of multiple connections), it may be possible to create those connections with a single request, and/or with multiple requests but with a single GUI action.

Figure 7H:
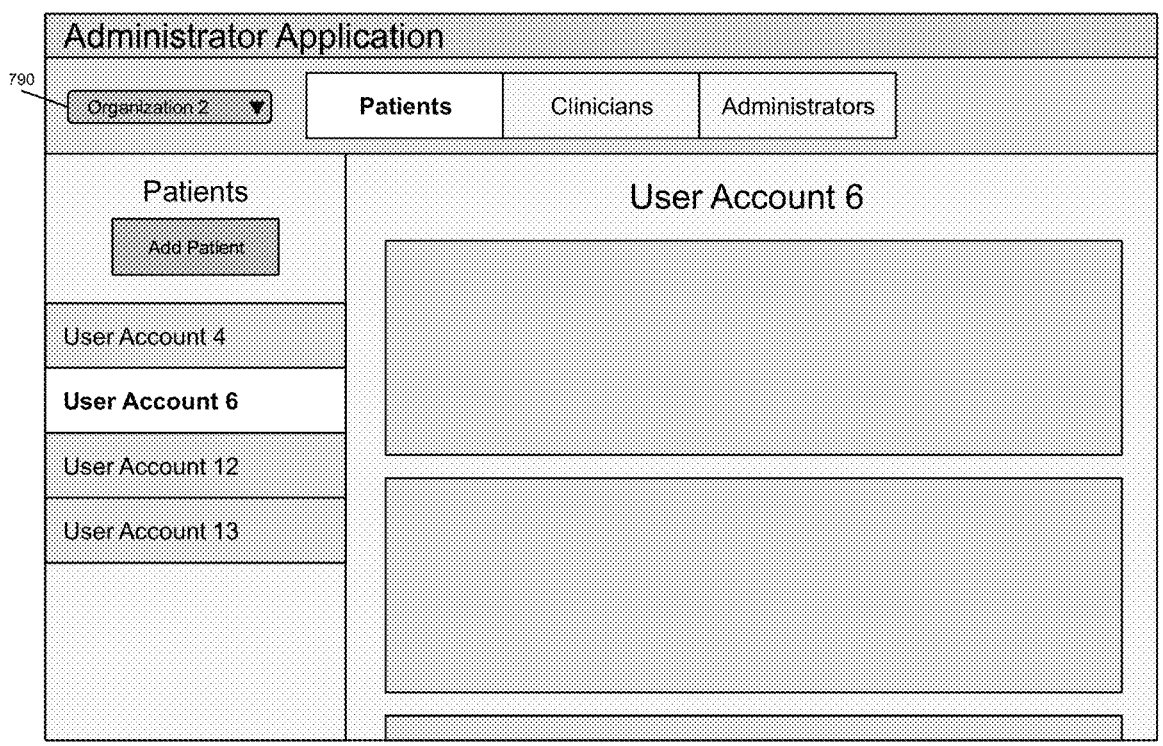

FIG. 7H illustrates an exemplary Administrator Application 700 in which the user has changed the organization with which the application is interfacing. The user has used GUI element 790 to have the Administrator Application 700 interface with Organization 2, whereas it previously interfaced with Organization 1. The user is utilizing their same user account to interact with the new organization, indicating that their user account may be connected to both Organization 1 and Organization 2 in the "administrator" role. In this illustration, the GUI for the Administrator Application 700 is the same when interfacing with Organization 2 as it is when interfacing with Organization 1, however that need not be the case. Organization 1 and Organization 2 may be the same kind of organization, or they may be different types of organizations. It should be noted that User Account 4, which has a "patient" connection to Organization 1 (as shown in FIG. 7A), also has a "patient" connection to Organization 2. Additionally, User Account 6, which has a "provider" connection to Organization 1 (as shown in FIG. 7D), has a "patient" connection to Organization 2.

The administrator using the Administrator Application 700 in FIGS. 7A-H may be able to remove any of the connections of the user accounts connected to Organization 1 and/or Organization 2. In some embodiments, any of the connected parties may remove a connection, whereas in other embodiments only certain parties may remove a connection. FIGS. 6A-H illustrate only one possible application and set of GUIs that interact with the account connection system. There may be any number of other possible applications, GUIs, and other embodiments. Further, an exemplary application may have any number of other characteristics and/or functionality, including but not limited to calendars, scheduling, videoconferencing, audio calls, text communications, referral management, directories, data visualization dashboards, payment and billing systems, auditing, form submissions, user account settings, educational content, remote patient monitoring, treatment plans, notes, goal setting, reminders, support groups, and additional forms of connections (to other organizations, devices, parent organizations, etc.). Applications may provide services used by many user accounts, some or all of which can interact with the other user accounts involved in those services, without each of the user accounts being connected to the other user accounts.

Figure 8:
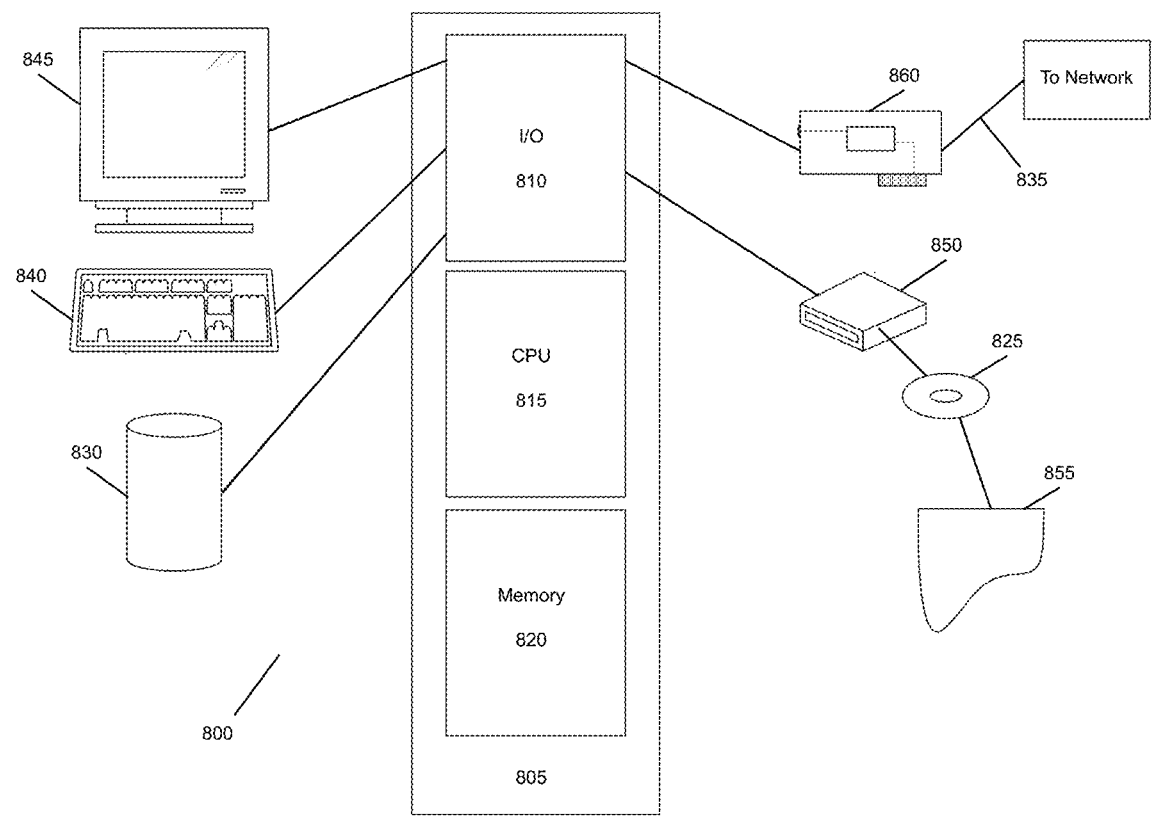
FIG. 8 illustrates an example computing system that may implement various systems.

FIG. 8 illustrates an example computing system 800 that may implement various systems, such as a user device 175, an application system 100, and the methods discussed herein. A general purpose computer system 800 is capable of executing a computer program product to execute a computer process. Data and program files may be input to the computer system 800, which reads the files and executes the programs therein such as the account connection system. Some of the elements of a general purpose computer system 800 are shown in FIG. 8 wherein a processor 805 is shown having an input/output (I/O) section 810, a central processing unit (CPU) 815, and a memory section 820. There may be one or more processors 805, such that the processor 805 of the computer system 800 comprises a single CPU 815, or a plurality of processing units, commonly referred to as a parallel processing environment. The computer system 800 may be a conventional computer, a server, a distributed computer, or any other type of computer, such as one or more external computers made available via a cloud computing architecture. The presently described technology is optionally implemented in software devices loaded in memory 820, stored on a configured DVD/CD-ROM 825 or storage unit 830, and/or communicated via a wired or wireless network link 835, thereby transforming the computer system 800 in FIG. 8 to a special purpose machine for implementing the described operations.

The memory section 820 may be volatile media, nonvolatile media, removable media, non-removable media, and/or other media or mediums that can be accessed by a general purpose or special purpose computing device. For example, the memory section 820 may include non-transitory computer storage media and communication media. Non-transitory computer storage media further may include volatile, nonvolatile, removable, and/or non-removable media implemented in a method or technology for the storage (and retrieval) of information, such as computer/machine-readable/executable instructions, data and data structures, engines, program modules, and/or other data. Communication media may, for example, embody computer/machine-readable/executable, data structures, program modules, algorithms, and/or other data. The communication media may also include an information delivery technology. The communication media may include wired and/or wireless connections and technologies and be used to transmit and/or receive wired and/or wireless communications.

The I/O section 810 is connected to one or more user-interface devices (e.g., a keyboard 840 and a display unit 845), a disc storage unit 830, and a disc drive unit 850. Generally, the disc drive unit 850 is a DVD/CD-ROM drive unit capable of reading the DVD/CD-ROM medium 825, which typically contains programs and data 855. Computer program products containing mechanisms to effectuate the systems and methods in accordance with the presently described technology may reside in the memory section 820, on a disc storage unit 830, on the DVD/CD-ROM medium 825 of the computer system 800, or on external storage devices made available via a cloud computing architecture with such computer program products, including one or more database management products, web server products, application server products, and/or other additional software components. Alternatively, a disc drive unit 850 may be replaced or supplemented by another storage medium drive unit. The network adapter 860 is capable of connecting the computer system 800 to a network via the network link 835, through which the computer system can receive instructions and data. Examples of such systems include personal computers, Intel or PowerPC-based computing systems, AMD-based computing systems, ARM-based computing systems, and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, and the like.

When used in a LAN-networking environment, the computer system 800 is connected (by wired connection and/or wirelessly) to a local network through the network interface or adapter 860, which is one type of communications device. When used in a WAN-networking environment, the computer system 800 typically includes a modem, a network adapter, or any other type of communications device for establishing communications over the wide area network. In a networked environment, program modules depicted relative to the computer system 800 or portions thereof, may be stored in a remote memory storage device. It is appreciated that the network connections shown are examples of communications devices for and other means of establishing a communications link between the computers may be used.

In an example implementation, source code executed by the at least one user device 175, source code executed by the at least one application system 100, a plurality of internal and external databases, source databases, and/or cached data on servers are stored in memory of the client computing device 175, memory of the backend system 105, or other storage systems, such as the disk storage unit 830 or the DVD/CD-ROM medium 825, and/or other external storage devices made available and accessible via a network architecture. The source code executed by the client computing device 175, the backend system 105, and/or the application system 100 may be embodied by instructions stored on such storage systems and executed by the processor 805.

Some or all of the operations described herein may be performed by the processor 805, which is hardware. Further, local computing systems, remote data sources and/or services, and other associated logic represent firmware, hardware, and/or software configured to control operations of the application system 100 and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 805 and a user may interact with a Graphical User Interface (GUI) using one or more user-interface devices (e.g., the keyboard 840, the display unit 845, and other user-interface devices in communication with the I/O section 810) with some of the data in use directly coming from online sources and data stores. The system set forth in FIG. 8 is but one possible example of a computer system that may be employed or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon executable instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, magnetic storage medium, optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A system, comprising:
   at least one computing device;
   and at least one memory containing instructions that, when executed, cause the at least one computing device to:
   receive a first connection request to create a first connection between user account and a specified entity;
   connect the user account with the specified entity by associating a unique identifier of the user account with a unique identifier of the specified entity based on the first connection request;
   establish, for the first connection, rules for operations relating to the user account and the specified entity relating to at least one of the user account, the specified entity, another entity, a service associated with an application system, or an application associated with the application system;

enable, in response to establishing the rules for operations and based on a role of the user account with respect to the specified entity, a new application feature, in the application associated with the application system for the user account, that relates to the specified entity;

receive a second connection request to create a second connection between the user account and a second specified entity;

connect the user account with the second specified entity by associating the unique identifier of the user account with a unique identifier of the second specified entity based on the second connection request;

establish, for the second connection, second rules for operations relating to the user account and the second specified entity relating to at least one of the user account, the second specified entity, another entity, a second service associated with an application system, or a second application associated with the application system;

and enable, in response to establishing the second rules for operations and based on a second role of the user account with respect to the second specified entity, a second new application feature, in the application for the user account, that relates to the second specified entity.

2. The system of claim 1, wherein each entity is associated with a unique identifier, and the unique identifier of a user account is associated with the unique identifier of the specified entity by updating one or more application system databases.

3. The system of claim 1, wherein the instructions, when executed, further cause the at least one computing device to:
receive a transmission request corresponding to at least one of:
requests from the user account to interact with data associated with the specified entity, requests from the user account to send data to the specified entity, requests from the specified entity to interact with data associated with the user account, or requests from the specified entity to send data to the user account; and
transmit, in response to the transmission request, data referenced in the transmission request, to be handled by the application system.

4. The system of claim 1, wherein the instructions, when executed, further cause the at least one computing device to:
receive an update request to update services that are part of the application to reflect the connection between the user account and the specified entity; and
execute, in response to the update request, any relevant actions stored in the instructions of the at least one computing device.

5. The system of claim 1, wherein a graphical user interface of the application displays modified features, functionality, information, and interactions reflective of at least one of the nature of the connection, the user account, the specified entity, or the application.

6. The system of claim 1, wherein the instructions, when executed, further cause the at least one computing device to:
allow, based on the rules for operations, the connection of the user account and the specified entity to be initiated by a third party, or allow, based on the rules for operations, the connection of the user account and the specified entity to be initiated by either the user account or the specified entity.

7. The system of claim 1, wherein the user account is not allowed to connect to the specified entity when the rules for operations do not support the connection.

8. The system of claim 1, wherein the instructions, when executed, further cause the at least one computing device to:
require approval by at least one of the user account or the specified entity to complete the connection;
receive the connection request to connect the user account and the specified entity such that the presence of the connection establishes the rules for operations;
establish, in response to the connection request, the connection as pending until at least one of the user account or the specified entity approves the connection;
complete the connection between the user account and the specified entity in response to receiving an approval request; and
cancel the connection between the user account and the specified entity in response to receiving a rejection request.

9. The system of claim 1, wherein the instructions, when executed, further cause the at least one computing device to:
receive a removal request to remove the connection between the user account and the specified entity;
remove, in response to the removal request, the connection between the user account and the specified entity;
revoke, in response to the removal request, permissions granted by the removed connection for the user account to interact with data associated with the specified entity;
revoke, in response to the removal request, permissions granted by the removed connection for the specified entity to interact with data associated with the user account;
update, in response to the removal request, services that are part of the one or more associated application systems to reflect the removed connection between the user account and the specified entity;
execute, in response to the update of services that are part of the one or more associated application systems, any relevant instructions stored on the at least one computing device; and
update, in response to the removal request, a graphical user interface of applications associated with at least one of the user account or the specified entity to reflect the removed connection.

10. The system of claim 1, wherein the user account establishes a plurality of connections with the specified entity, wherein each of the plurality of connections establishes different rules for the operations of the one or more associated application systems, and the plurality of connections result from data associated with at least one of the user account or the specified entity.

11. The system of claim 1, wherein the instructions, when executed, further cause the at least one computing device to:
receive a third connection request to connect a second user account and a third specified entity such that the presence of the second connection establishes rules for operations relating to at least one of the second user account, the third specified entity, another entity, the service associated with the application system, or the application associated with the application system; and
connect the second user account with the third specified entity by associating a unique identifier of the second user account with a unique identifier of the third specified entity based on the third connection request.

12. A method for handling the connection of user accounts to other entities performed by one or more computing devices, comprising the steps of:
receiving a first connection request to create a first connection between user account and a specified entity;
connecting the user account with the specified entity by associating a unique identifier of the user account with a unique identifier of the specified entity based on the first connection request;
establishing rules for operations relating to the user account and the specified entity relating to at least one of the user account, the specified entity, another entity, a service provided by the specified entity, or an application associated with an application system;
enabling, in response to establishing the rules for operations, a new application feature in the application associated with the application system for the user account based on a role of the user account with respect to the specified entity;
receiving a second connection request to create a second connection between the user account and a second specified entity;
connecting the user account with the second specified entity by associating the unique identifier of the user account with a unique identifier of the second specified entity based on the second connection request;
establishing, for the second connection, second rules for operations relating to the user account and the second specified entity relating to at least one of the user account, the second specified entity, another entity, a second service associated with an application system, or a second application associated with the application system;
and enabling, in response to establishing the second rules for operations and based on a second role of the user account with respect to the second specified entity, a second new application feature, in the application for the user account, that relates to the second specified entity.

13. The method of claim 12, wherein each entity is associated with a unique identifier, and the unique identifier of the user account is associated with the unique identifier of the specified entity by updating one or more application system databases.

14. The method of claim 12, wherein the instructions, when executed, further cause the at least one computing device to:
receive a transmission request corresponding to at least one of:
requests from the user account to interact with data associated with the specified entity, requests from the user account to send data to the specified entity, requests from the specified entity to interact with data associated with the user account, or requests from the specified entity to send data to the user account; and
transmit, in response to the transmission request, data referenced in the transmission request, to be handled by the application system.

15. The method of claim 12, wherein the instructions, when executed, further cause the at least one computing device to:
receive an update request to update services that are part of the application to reflect the connection between the user account and the specified entity; and
execute, in response to the update request, any relevant actions stored in the instructions of the at least one computing device.

16. The method of claim 12, wherein a graphical user interface of the application displays modified features, functionality, information, and interactions reflective of at least one of the nature of the connection, the user account, the specified entity, or the application.

17. The method of claim 12, wherein the instructions, when executed, further cause the at least one computing device to:
allow, based on the rules for operations, the connection of the user account and the specified entity to be initiated by a third party, or allow, based on the rules for operations, the connection of the user account and the specified entity to be initiated by either the user account or the specified entity.

18. The method of claim 12, wherein the user account is not allowed to connect to the specified entity when the rules for operations do not support the connection.

19. The method of claim 12, wherein the instructions, when executed, further cause the at least one computing device to:
require approval by at least one of the user account and/or or the specified entity to complete the connection;
receive the connection request to connect the user account and the specified entity such that the presence of the connection establishes the rules for operations;
establish, in response to the connection request, the connection as pending until at least one of the user account or the specified entity approves the connection;
complete the connection between the user account and the specified entity in response to receiving an approval request; and
cancel the connection between the user account and the specified entity in response to receiving a rejection request.

20. The method of claim 12, wherein the instructions, when executed, further cause the at least one computing device to:
receive a removal request to remove the connection between the user account and the specified entity;
remove, in response to the removal request, the connection between the user account and the specified entity;
revoke, in response to the removal request, permissions granted by the removed connection for the user account to interact with data associated with the specified entity;
revoke, in response to the removal request, permissions granted by the removed connection for the specified entity to interact with data associated with the user account;
update, in response to the removal request, services that are part of the one or more associated application systems to reflect the removed connection between the user account and the specified entity;
execute, in response to the update of services that are part of the one or more associated application systems, any relevant instructions stored on the at least one computing device; and
update, in response to the removal request, a graphical user interface of applications associated with at least one of the user account or the specified entity to reflect the removed connection.

21. The method of claim 12, wherein the user account establishes a plurality of connections with the specified entity, wherein each of the plurality of connections establishes different rules for the operations of the one or more associated application systems, and the plurality of connections result from data associated with at least one of the user account or the specified entity.

22. The method of claim 12, wherein the instructions, when executed, further cause the at least one computing device to:
   receive a third connection request to connect a second user account and a third specified entity such that the presence of the third connection establishes rules for operations relating to at least one of the second user account, the third specified entity, another entity, the service associated with the application system, or the application associated with the application system; and
   connect the second user account with the third specified entity by associating a unique identifier of the second user account with a unique identifier of the third specified entity based on the third connection request.

23. At least one non-transitory computer readable medium storing instructions that, upon being executed by one or more processors, cause the one or more processors to:
   receive a first connection request to create a first connection between a user account and a specified entity;
   connect the user account with the specified entity by associating a unique identifier of the user account with a unique identifier of the specified entity based on the connection request;
   establish rules for operations relating to the user account and the specified entity relating to at least one of the user account, the specified entity, another entity, a service associated with an application system, or an application associated with the application system;
   enable, in response to establishing the rules for operations and based on a role of the user account with respect to the specified entity, a new application feature, in the application associated with the application system for the user account, that relates to the specified entity;
   receive a second connection request to create a second connection between the user account and a second specified entity;
   connect the user account with the second specified entity by associating the unique identifier of the user account with a unique identifier of the second specified entity based on the second connection request;
   establish, for the second connection, second rules for operations relating to the user account and the second specified entity relating to at least one of the user account, the second specified entity, another entity, a second service associated with an application system, or a second application associated with the application system;
   and enable, in response to establishing the second rules for operations and based on a second role of the user account with respect to the second specified entity, a second new application feature, in the application for the user account, that relates to the second specified entity.

24. The at least one non-transitory computer readable medium of claim 23, wherein each entity is associated with a unique identifier, and the unique identifier of a user account is associated with the unique identifier of the specified entity by updating one or more application system databases.

25. The at least one non-transitory computer readable medium of claim 23, wherein the instructions, when executed, further cause the at least one computing device to:
   receive a transmission request corresponding to at least one of:
      requests from the user account to interact with data associated with the specified entity, requests from the user account to send data to the specified entity, requests from the specified entity to interact with data associated with the user account, requests from the specified entity to send data to the user account; and
   transmit, in response to the transmission request, data referenced in the transmission request, to be handled by the application system.

26. The at least one non-transitory computer readable medium of claim 23, wherein the instructions, when executed, further cause the at least one computing device to:
   receive an update request to update services that are part of the application system to reflect the connection between the user account and the specified entity; and
   execute, in response to the update request, any relevant actions stored in the instructions of the at least one computing device.

27. The at least one non-transitory computer readable medium of claim 23, wherein a graphical user interface of the application displays modified features, functionality, information, and interactions reflective of at least one of the nature of the connection, the user account, the specified entity, or the application.

28. The at least one non-transitory computer readable medium of claim 23, wherein the instructions, when executed, further cause the at least one computing device to:
   allow, based on the rules for operations, the connection of the user account and the specified entity to be initiated by a third party, or allow, based on the rules for operations, the connection of the user account and the specified entity to be initiated by either the user account or the specified entity.

29. The at least one non-transitory computer readable medium of claim 23, wherein the user account is not allowed to connect to the specified entity when the rules for operations do not support the connection.

30. The at least one non-transitory computer readable medium of claim 23, wherein the instructions, when executed, further cause the at least one computing device to:
   require approval by at least one of the user account or the specified entity to complete the connection;
   receive the connection request to connect the user account and the specified entity such that the presence of the connection establishes the rules for operations;
   establish, in response to the connection request, the connection as pending until at least one of the user account or the specified entity approves the connection;
   complete the connection between the user account and the specified entity in response to receiving an approval request; and
   cancel the connection between the user account and the specified entity in response to receiving a rejection request.

31. The at least one non-transitory computer readable medium of claim 23, wherein the instructions, when executed, further cause the at least one computing device to:
   receive a removal request to remove the connection between the user account and the specified entity;
   remove, in response to the removal request, the connection between the user account and the specified entity;
   revoke, in response to the removal request, permissions granted by the removed connection for the user account to interact with data associated with the specified entity;

revoke, in response to the removal request, permissions granted by the removed connection for the specified entity to interact with data associated with the user account;

update, in response to the removal request, services that are part of the one or more associated application systems to reflect the removed connection between the user account and the specified entity;

execute, in response to the update of services that are part of the one or more associated application systems, any relevant instructions stored on the at least one computing device; and update, in response to the removal request, a graphical user interface of applications associated with at least one of the user account or the specified entity to reflect the removed connection.

32. The at least one non-transitory computer readable medium of claim 23, wherein the user account establishes a plurality of connections with the specified entity, wherein each of the plurality of connections establishes different rules for the operations of the one or more associated application systems, and the plurality of connections result from data associated with at least one of the user account or the specified entity.

33. The at least one non-transitory computer readable medium of claim 23, wherein the instructions, when executed, further cause the at least one computing device to:

receive a third connection request to connect a second user account and a third specified entity such that the presence of the third connection establishes rules for operations relating to at least one of the second user account, the third specified entity, another entity, the service associated with the application system, or the application associated with the application system; and connect the second user account with the third specified entity by associating a unique identifier of the second user account with a unique identifier of the third specified entity based on the third connection request.

* * * * *